United States Patent
Rava et al.

(10) Patent No.: US 8,700,341 B2
(45) Date of Patent: Apr. 15, 2014

(54) PARTITION DEFINED DETECTION METHODS

(75) Inventors: Richard P. Rava, Redwood City, CA (US); Brian K. Rhees, Tracy, CA (US); John P. Burke, Reno, NV (US)

(73) Assignee: Verinata Health, Inc., Redwood City, CA (US)

( * ) Notice: Subject to any disclaimer, the term of this patent is extended or adjusted under 35 U.S.C. 154(b) by 339 days.

(21) Appl. No.: 13/009,708

(22) Filed: Jan. 19, 2011

(65) Prior Publication Data
US 2011/0177517 A1 Jul. 21, 2011

Related U.S. Application Data

(60) Provisional application No. 61/296,464, filed on Jan. 19, 2010.

(51) Int. Cl.
G01N 33/48 (2006.01)
G01N 33/50 (2006.01)
G01N 31/00 (2006.01)
G06F 19/12 (2011.01)

(52) U.S. Cl.
CPC .................................... G06F 19/12 (2013.01)
USPC ................................ 702/20; 702/19; 702/27

(58) Field of Classification Search
None
See application file for complete search history.

(56) References Cited

U.S. PATENT DOCUMENTS

| | | | |
|---|---|---|---|
| 5,888,740 A | 3/1999 | Han | |
| 6,403,315 B1 | 6/2002 | Drmanac | |
| 6,555,315 B1 * | 4/2003 | Short | 435/6.14 |
| 2007/0087345 A1 | 4/2007 | Olson-Munoz et al. | |
| 2007/0202525 A1 | 8/2007 | Quake et al. | |
| 2008/0070792 A1 | 3/2008 | Stoughton et al. | |
| 2008/0138809 A1 | 6/2008 | Kapur et al. | |
| 2008/0220422 A1 | 9/2008 | Shoemaker et al. | |
| 2009/0026082 A1 | 1/2009 | Rothberg et al. | |
| 2009/0029377 A1 | 1/2009 | Lo et al. | |
| 2009/0087847 A1 | 4/2009 | Lo et al. | |
| 2009/0098547 A1 | 4/2009 | Ghosh | |

(Continued)

FOREIGN PATENT DOCUMENTS

WO WO 2003/004677 1/2003
WO WO 2006/028152 A1 * 3/2006

(Continued)

OTHER PUBLICATIONS

International Search Report, dated Mar. 9, 2011, issued in corresponding International Application No. PCT/US2011/021751.

(Continued)

Primary Examiner — Russell S Negin
(74) Attorney, Agent, or Firm — Weaver Austin Villeneuve & Sampson LLP

(57) ABSTRACT

Methods are disclosed for resolving measurement problems such problems in measuring chromosomal copy number. Some disclosed methods involve first selecting a primary assay element characteristic to partition. Such characteristic may be a source of experimental variability such as the GC content of measured DNA sequences. Additionally, the disclosed methods may employ an abundance or copy number function to transform the assay element frequencies into an abundance, dose, copy number score, or the like. In some cases, the disclosed methods estimate an amount of certain fetal DNA in a sample. The methods can further compare the estimated amount to a measured amount of fetal DNA in the sample. The comparison can be used to determine the fetal sex or aneuploidy.

32 Claims, 9 Drawing Sheets

(56) References Cited

U.S. PATENT DOCUMENTS

| | | | |
|---|---|---|---|
| 2010/0112590 A1* | 5/2010 | Lo et al. | 435/6 |
| 2010/0138165 A1 | 6/2010 | Fan et al. | |
| 2011/0003293 A1* | 1/2011 | Stoughton et al. | 435/6 |

FOREIGN PATENT DOCUMENTS

| | | |
|---|---|---|
| WO | WO 2006/028153 | 3/2006 |
| WO | WO 2007/147079 A2 * | 12/2007 |
| WO | WO 2010/033578 | 3/2010 |
| WO | WO 2011/091063 | 7/2011 |

OTHER PUBLICATIONS

Chiu et al., "Noninvasive prenatal diagnosis of fetal chromosomal aneuploidy by massively parallel genomic sequencing of DNA in maternal plasma," PNAS vol. 105, No. 51, pp. 20458-20463 (Dec. 23, 2008).

Chiu et al., "Non-invasive prenatal assessment of trisomy 21 by multiplexed maternal plasma DNA sequencing: large scale validity study," BMJ 2011; 342:c7401.

Fan et al., "Noninvasive diagnosis of fetal aneuploidy by shotgun sequencing DNA from maternal blood," PNAS vol. 105, No. 42, pp. 16266-16271, Oct. 21, 2008.

SantaLucia, John Jr., "A unified view of polymer, dumbbell, and oligonucleotide DNA nearest-neighbor thermodynamics," PNAS USA, vol. 95, pp. 1460-1465, Feb. 1998.

European Search Report date Jun. 3, 2013 for European Application No. 11735131.2.

Office Action dated Aug. 29, 2013 issued in Australian Patent Application No. 2011207561.

* cited by examiner

| FIG. 6A | FIG. 6B |

| T18 | | T13 | | T21 | | |
|---|---|---|---|---|---|---|
| 20091023 | 20091023 | 20091203 | 20091203 | 20091203 | 20090826 | 20090710 | 20091216 | 20091216 | 20091023 | 20091201 |
| 2.008 | 2.015 | 2.008 | 2.017 | 2.011 | 2.028 | 2.025 | 2.007 | 2.011 | 2.017 | 2.008 |
| 2.030 | 2.036 | 2.015 | 2.028 | 2.026 | 2.003 | 2.026 | 2.015 | 2.005 | 2.025 | 2.014 |
| 2.004 | 2.010 | 2.009 | 1.989 | 1.999 | 2.041 | 2.022 | 2.016 | 2.001 | 2.002 | 2.005 |
| 1.983 | 1.980 | 1.984 | 1.978 | 1.978 | 1.973 | 1.954 | 1.993 | 1.969 | 1.979 | 1.977 |
| 1.962 | 1.964 | 1.985 | 2.005 | 2.045 | 1.951 | 1.947 | 1.987 | 1.987 | 1.973 | 1.981 |
| 1.996 | 1.995 | 2.001 | 1.995 | 2.000 | 2.014 | 1.989 | 1.986 | 1.992 | 2.015 | 1.983 |
| 2.052 | 2.048 | 2.037 | 2.051 | 2.039 | 2.081 | 2.080 | 2.044 | 2.038 | 2.064 | 2.035 |
| 2.092 | 2.072 | 2.071 | 2.056 | 2.063 | 2.200 | 2.138 | 2.064 | 2.054 | 2.090 | 2.067 |
| 2.076 | 2.061 | 2.035 | 2.053 | 2.050 | 2.151 | 2.120 | 2.050 | 2.056 | 2.081 | 2.063 |
| 2.043 | 2.021 | 2.069 | 2.020 | 2.022 | 2.005 | 1.999 | 2.027 | 2.014 | 2.014 | 2.013 |
| 2.035 | 2.048 | 2.016 | 1.988 | 2.025 | 2.282 | 2.094 | 2.028 | 1.982 | 2.057 | 2.014 |
| 1.993 | 1.995 | 2.005 | 2.001 | 1.997 | 1.989 | 1.977 | 2.006 | 2.005 | 1.998 | 1.994 |
| 2.100 | 2.078 | 2.072 | 2.090 | 2.069 | 2.118 | 2.131 | 2.072 | 2.073 | 2.085 | 2.073 |
| 2.017 | 2.049 | 1.997 | 2.018 | 2.002 | 2.437 | 2.078 | 2.078 | 2.085 | 2.073 | 2.157 |
| 2.112 | 2.124 | 2.074 | 2.113 | 2.089 | 2.263 | 2.213 | 2.110 | 2.077 | 2.143 | 2.101 |
| 1.876 | 1.975 | 1.988 | 1.975 | 1.982 | 1.970 | 1.953 | 1.983 | 1.982 | 1.979 | 1.986 |
| 1.926 | 1.921 | 1.942 | 1.944 | 1.936 | 1.917 | 1.883 | 1.946 | 1.963 | 1.923 | 1.951 |
| 1.976 | 1.973 | 1.986 | 1.984 | 2.001 | 1.978 | 1.957 | 1.984 | 1.986 | 1.988 | 1.978 |
| 1.979 | 1.981 | 1.990 | 1.991 | 1.983 | 1.954 | 1.970 | 1.979 | 1.988 | 1.975 | 1.984 |
| 1.986 | 1.991 | 1.984 | 1.976 | 1.982 | 1.986 | 1.984 | 1.991 | 1.981 | 1.997 | 1.991 |
| 2.012 | 1.998 | 2.009 | 2.006 | 2.009 | 1.995 | 1.981 | 2.004 | 2.012 | 1.998 | 1.998 |
| 2.007 | 2.012 | 2.018 | 2.017 | 2.032 | 2.040 | 2.016 | 2.010 | 2.010 | 2.011 | 2.017 |
| -1#IND | -1#IND | -1#IND | -1#IND | -1#IND | -1#IND | -1#IND | -1#IND | -1#IND | -1#IND | -1#IND |
| 1.957 | 1.978 | 1.938 | 1.971 | 1.916 | 1.264 | 1.959 | 1.934 | 1.979 | 1.914 | 1.968 |
| -1#IND | -1#IND | -1#IND | -1#IND | -1#IND | -1#IND | -1#IND | -1#IND | -1#IND | -1#IND | -1#IND |

PARTITION DEFINED DETECTION METHODS

CROSS-REFERENCE TO RELATED APPLICATIONS

This application claims benefit under 35 U.S.C. §119(e) of U.S. Provisional Patent Application No. 61/296,464, filed Jan. 19, 2010, naming J. Burke and R. Rava as inventors. U.S. Provisional Patent Application No. 61/296,464 is incorporated herein by reference in its entirety and for all purposes.

BACKGROUND

It is often desirable to measure the abundance or relative concentration of biological analytes. Such analytes include, for example, chromosomes, genome sequences, mRNAs, peptides, compounds, genotypes, or haplotypes. Experimental techniques for making such measurements may introduce biases, which if unaccounted for can artificial skew results.

A drawback of existing methods is that they frequently fail to account for inter experiment or batch variability caused by differing coverage of assay elements between experiments, experiments, or runs. Differing samplings of such assay elements are the result of chance or systemic factors such as environment, differing experimental application, or other factors. For example, in the case of measuring chromosome abundance, the GC content of sampled nucleic acid sequences of different chromosomes may bias chromosome abundance measurements suggesting an aberration in chromosome abundance even when no real change in chromosome abundance has occurred. (GC content is the percentage or ratio of guanine and cytosine in all nitrogenous bases in a nucleic acid.)

For these reasons, improved techniques for addressing experimental variability in biological assays are desirable.

SUMMARY

The present invention provides a family of methods to resolve such measurement issues in general and the chromosomal copy number problem in particular. Some disclosed methods detecting a trait involve first selecting a primary assay element characteristic to partition. Such characteristic may be a source of experimental variability such as the GC content of measured DNA sequences. After selecting an appropriate partition, the methods calculate an expectation value for the trait. The expectation value is calculated from partitioned test results using a relationship including an assumption about the physical character of the trait (e.g., there will be two copies of chromosome 21). The expectation value is compared to an actual measured value (e.g., the number of measured sequence tags that map to chromosome 21) to determine whether the sample being tested conforms to the assumption about the physical characteristics of the trait. Additionally, the disclosed methods may employ an abundance or copy number function to transform the measure value or frequency into an abundance, dose, copy number score, or the like.

In some cases, the disclosed methods estimate an amount of fetal DNA in a sample. The methods can further comprise comparing the amount to an estimated amount of fetal DNA in the sample. The trait can be fetal sex or aneuploidy.

In certain embodiments, disclosed methods of detecting aneuploidy or sex in a fetus may be characterized by the following operations: (a) extracting DNA from the blood of an individual carrying the fetus; (b) mapping segments (sometimes called sequence tags) of the extracted DNA to at least a chromosome of interest in a genome; (c) partitioning the segments on the basis of a source of experimental variability; (d) calculating an expected number of segments mapping to the chromosome of interest; and (e) detecting aneuploidy or sex in the fetus by comparing an actual number of segments mapping to the chromosome of interest against the expected number of segments mapping to the chromosome of interest. Calculating the expected number of segments accounts for the experimental variability by using the partitioning. Further, the calculation assumes that the expected number of segments is based on an assumption about chromosome type and number (e.g., an assumption that the chromosome under consideration exhibits normal ploidy).

In various implementations, the methods involve PCR amplifying the segments before their mapping in (b). Thus, the source of variability may be chosen to reflect the ease with which the segments are amplified by an amplification technique applied to the extracted DNA. For example, the source of experimental variability may be the GC content of the segments. In other embodiments, the source of experimental variability is the methylation state of nucleotides in a sequence.

In various embodiments, calculating the expected number of segments involves summing the products of (i) a number of segments generated from the extracted DNA and (ii) a ratio of substrings in the chromosome of interest to substrings in the entire genome, over a range of partition levels for the number of segments generated and the ratio. Note that this ratio may assume normal ploidy or some other physical characteristics of the chromosome and/or genome. Further, in a specific embodiment, the partition levels may be provided for different levels of GC content in the segments. In one example, the expected number of segments is given by the following expression:

$$E(\#R) = \Sigma_{\forall i \in P(G)/ni} |R_i|/|G_i|$$

wherein
$E(\#R)$ is the expected number of segments,
$P(G)$ is all partition levels in the genome,
$n_i$ is the number of generated segments from the extracted DNA assigned to a partition i,
$|R_i|$ is the number of substrings within the chromosome of interest that are assigned to partition i, and
$|G_i|$ is the number of substrings within the entire genome that are assigned to partition i.

In certain embodiments, detecting aneuploidy or sex in the fetus involves providing the comparison of the actual number of segments mapping to the chromosome of interest against the expected number of segments mapping to the chromosome of interest in the form of a z-score or other metric that facilitates specifying the detection in terms of confidence levels. In various embodiments, the methods may also include performing an internal control by comparing segments or a count or score of the segments mapped to the chromosome of interest against a different count or score of the segments mapped to a different chromosome of the extracted DNA.

In some embodiments, detecting aneuploidy or sex in the fetus involves providing the comparison of the actual number of segments mapping to the chromosome of interest against the expected number of segments mapping to the chromosome of interest in a form that includes trained parameters to, e.g., account for a fixed bias in the methods associated with mapping segments. For example, the trained parameters may be a sample center and a sample spread. In a specific example, the trained parameters are obtained from samples taken from females carrying fetuses without aneuploidy.

In some cases, mapping the segments of the extracted DNA is conducted without distinguishing maternal and fetal origin DNA. In some implementations, the segments all have the same length (e.g., at least 30 base pairs).

Another aspect of the invention pertains to computer program products including machine-readable media on which are stored program instructions for implementing at least some portion of the methods described above. The machine readable media may be tangible and/or non-transitory. Any of the methods disclosed herein may be represented, in whole or in part, as program instructions that can be provided on such computer readable media. In addition, the invention pertains to various combinations of data and associated data structures generated and/or used as described herein.

These and other features will be described in more detail below with reference to the associated drawings.

DETAILED DESCRIPTION

Introduction and Overview

Figure 1A:
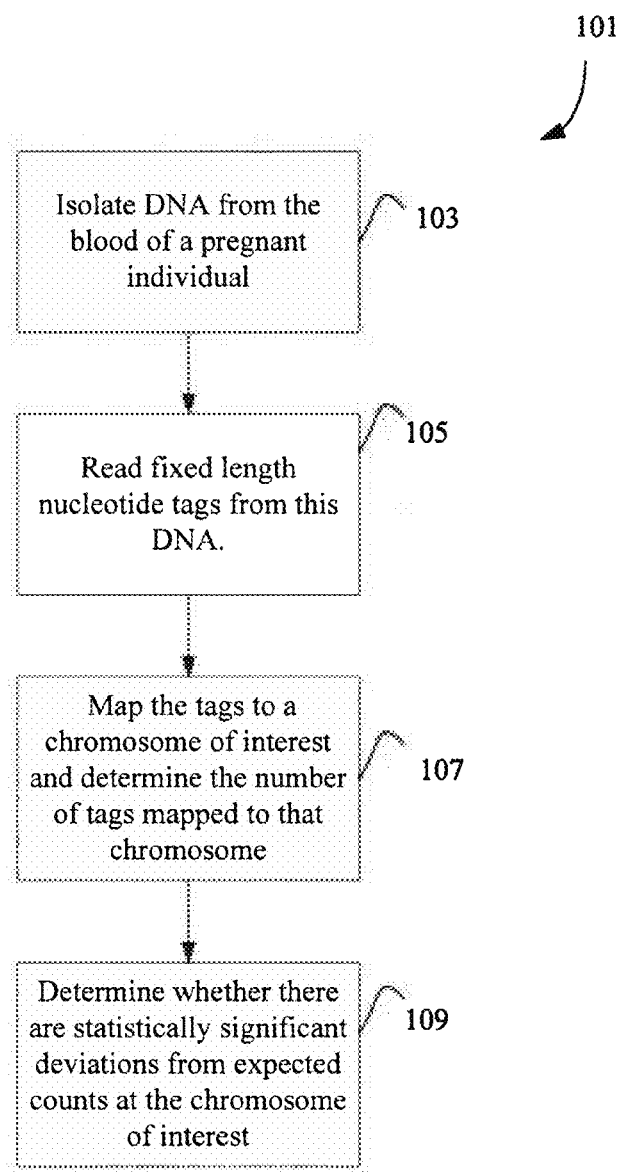
FIG. 1A is a flow chart depicting a generalized method for detecting information about a chromosome by using a blood sample from a pregnant individual.

Modern biological assays often involve multiple assay elements in the measurement of a single analyte. Inter-experiment variability is produced when assay elements are heterogeneous and experiment replicates of sample assay elements behave differently due to environmental or other nuisance factors not related to the biological conditions of interest. Consider the generation of short sequences to distinguish cases where three copies of human chromosome 21 are present (a feature associated with Down's syndrome and called trisomy 21 or T21) from the normal case with only two copies. It is often not possible to establish a single threshold to discriminate T21 from normal cases with convenient metrics, e.g., number of chromosome 21 sequences per number of chromosome 1 sequences, because environmental, batch, or other factors, bias sequence generation. Such biasing factors can include, e.g., the effect of GC content on polymerase chain reaction (PCR) amplification or nucleic acid processing operation.

Some embodiments disclosed herein reduce this inter-experiment variability by partitioning directly measurable factor (a source of experimental variation such as GC content) and then providing an abundance score using the sampling frequency of the partitioned assay elements in an individual experiment. In many cases, the methods define the partitioned assay elements in terms of a nucleotide base content (e.g., GC content) of the target chromosomal sequence. An experimental sample pattern can be defined to be the often random spatial match of individual sequences to chromosome locations. One summary statistic that combines the chromosome base and the sampling pattern employs the weighted GC content of chromosomal regions covered by generated sequences, which can also be calculated as the GC content of the measured sequences themselves.

In fact, many implementations of the disclosed methods are particularly concerned with addressing biases in a nucleic acid tag sequence numbers resulting from the GC content of DNA sequences derived from a sample. For a typical source of nucleic acid, one might assume that on average 50% of any given sequence is attributable to GC content. However, due to random and non-random variations in nature, various DNA sequences have significantly more or less than 50% GC content. Some sequencing processes introduce a bias toward GC rich regions during, e.g., amplification. The impact on amplification is a manifestation of the variability in PCR which results from variability in the melting temperature of DNA strands as a function of GC content. That is, the efficiency of PCR amplification depends on the GC content of the sequences amplified, e.g., a sequence with greater GC content may amplify more efficiently than a sequence with lesser GC content. If left unaccounted for, this bias would give artificially high counts for GC rich sequences and artificially low counts for GC poor sequences.

Thus, in accordance with various embodiments described herein, the GC content of each amplified sequence is used to normalize the amount of the sequence detected in the sample. Of course, other sources of experimental variability can be accounted for employing the techniques of the present invention. These include, for example, the methylation state of the sequences, the length of the sequences, duplex melting temperature, regions or sequences that perform well with PCR or sequencing and those that do not, and the like.

Regarding the example of GC content, one of skill will appreciate that both TA content and GC content can be used for the methods of the invention. For example, % GC content can be expressed as 100%–% TA content. A model of sequence based composition can capture these concepts and other measures of sequence content, e.g., fraction of individual nucleotides (e.g., C content, T content, A content, G content, U content, etc), fraction of pyrimidines (e.g., cytosine (C), thymine (T), and uracil (U)) or purines (e.g., adenine (A) and guanine (G)), fraction natural versus non-natural nucleic acids, fraction methylated nucleotides, CpG content, etc.

Various embodiments described herein, detect a trait under consideration (e.g., ploidy of particular human chromosomes) by comparing a measured value reflecting that trait (e.g., number of DNA sample sequence tags mapping to a particular chromosome) and an expected value for the measurement. The expected value has at least two salient properties: (i) it accounts for a source of experimental variability (e.g., GC content) and (ii) it assumes a particular biological characteristic (e.g., normal ploidy). The comparison of the measured and expected values can be provided in any of a number of formats, some of which are outlined below. In some cases, the comparison is provided z-scored or other statistically meaningful form to facilitate detection of aberrations in the trait under consideration (e.g., aneuploidy).

The following description of a detection method for trisomy 21 illustrates some aspects of the invention. It employs an expectation number that accounts for the GC bias in amplification. It partitions sequences and generated tags by GC content. It should be understood that the invention is not limited to this trait (trisomy 21) or this source of experimental variability (GC content). Various pertinent aspects of the invention are discussed more generally in the sections below, particularly the section titled "Calculations employing Partition Methods."

In the T21 example, a nucleic acid sample containing DNA of a fetus being tested for T21 is amplified and physically sequenced into a plurality of segments or tags, each of which may be the same length (e.g., 36 nucleotides). Methods for determining fetal aneuploidy by generation and mapping of sequence tags have been previously described (Fan et al., PNAS 105:16266-16271 (2008); Chiu et al. PNAS 105: 20458-20463 (2008); Chiu et al., BMJ 2011; 342:c7401 (2011); US Patent Publication Nos. 2007/0202525 filed Feb. 2, 2007, 2010/0138165 filed Jan. 29, 2010, 2009/0029377 filed Jul. 23, 2008, 2010/0112590 filed Nov. 6, 2009, and pending U.S. patent application Ser. Nos. 12/958,352 filed Dec. 1, 2010 and 12/958,353 filed Dec. 1, 2010), each incorporated herein by reference.

Each of these generated tags is directly mapped to one of the 23 human chromosomes to generate a number of mapped tags for each chromosome. Additionally, the mapped tags are partitioned based on their GC content. For example, some of the mapped tags will be contained in a partition having 14 out of 36 base positions occupied by guanine or cytosine; other mapped tags will be contained in a partition having 15 out of 36 base positions occupied by guanine or cytosine; still other mapped tags will be contained in a partition having 16 out of 36 base positions occupied by guanine or cytosine; and so on. This partitioning is performed for all generated tags, not just those mapping to chromosome 21.

Additionally, given knowledge about the nucleotide sequence of the human genome, including each of its chromosomes, the method is provided with a list of all the possible 36mer substrings in chromosome 21. These substrings are partitioned based on their GC content as were the generated segments generated in the test. The method is further provided with a list of all the possible 36mer substrings in the entire human genome (all 23 chromosomes) and these genome substrings are partitioned based on their GC content as well.

With this information—the GC partitioned generated tags, chromosome 21 substrings, and genomic substrings—the method can determine an expectation number of generated tags mapping to chromosome 21 that (i) accounts for GC amplification bias, and (ii) assumes two copies of chromosome 21. If the actual number of generated tags mapping to chromosome 21 (as directly determined from the sample) is significantly greater than the calculated expectation number, then one can assume that the test to T21 is positive.

In various embodiments, the expectation value is calculated by summing over all partition levels (e.g., GC=0 to GC=36) a combination of the actually generated tags or segments (often represented herein as $n_i$) and an expected fraction of 36mer substrings in chromosome 21 (often generally represented herein as $|R_i|$) over all 36mer substrings in the genome (often represented herein as $|G_i|$). The expected fraction assumes that there are two copies of chromosome 21 and not three.

Thus, in this example, the expectation number of segments mapping to chromosome 21 may be mathematically represented as $$E(\#R) = \Sigma_{\forall i \in P(G)} n_i |R_i|/|G_i|$$

where P represents the partition levels (GC=0 to GC=36) and #R represents the number of generated segments mapping to chromosome 21.

The expected variance and other expected characteristics of the test results may also be calculated as explained generally in Calculations employing Partition Methods section below.

The comparison of the actual and expected tag numbers can be represented in various forms including a difference (e.g., #R−E(#R)) or a quotient (e.g., #R/E(#R)) or other formulations. Further, the comparison may be normalized, scaled, or otherwise transformed using techniques well understood in the art. For example, a value similar to a z-score can be determined for the tags mapping to chromosome 21. This may be represented as $$Z(R, P, G) = \frac{\#R - (\text{normal case } \#R \text{ center})}{(\text{normal case } \#R \text{ std dev})} \approx \frac{\#R - E(\#R)}{\sqrt{\text{Var}(\#R)}}$$

where $$\text{Var}(\#R) = \sum_{\forall i \in P(G)} \text{Var}(\#R_i) = \sum_{\forall i \in P(G)} \left[\frac{n_i |R_i|}{|G_i|}\left(1 - \frac{|R_i|}{|G_i|}\right)\right]$$

Additionally, the z-score or other form of comparison between the measured and expected tag numbers may incorporate trained parameters, such as values of the mean and spread for tag numbers taken from samples of females carrying normal fetuses. See the discussion associated with equation 6 below.

Note that the above example accounts for a source of experimental variability (GC content of segments) without incorporating any assumptions about the underlying experimental basis for that variability—other than the partitioned fraction of substrings in the chromosome of interest to substrings in the entire genome. For example, the calculations do not employ any explicit relationships between GC content and level of amplification. The technique does not make use of a linear or non-linear relationship reflecting how GC level in a DNA sequence, as an independent variable, influences the expected tag number in an experiment.

It is also worth noting that the expectation value is not calculated a priori, before an experiment is conducted, but only after the experiment itself is conducted. Specifically, the expectation value is a function of $n_i$, which is the number of generated sequences at partition level i. Thus, the experiment itself provides an internal correction for the experimental variability. This approach does not make any assumptions about the form of the relationship between GC content and level of amplification or more generally the expected number of tags.

Figures 6, 6A:
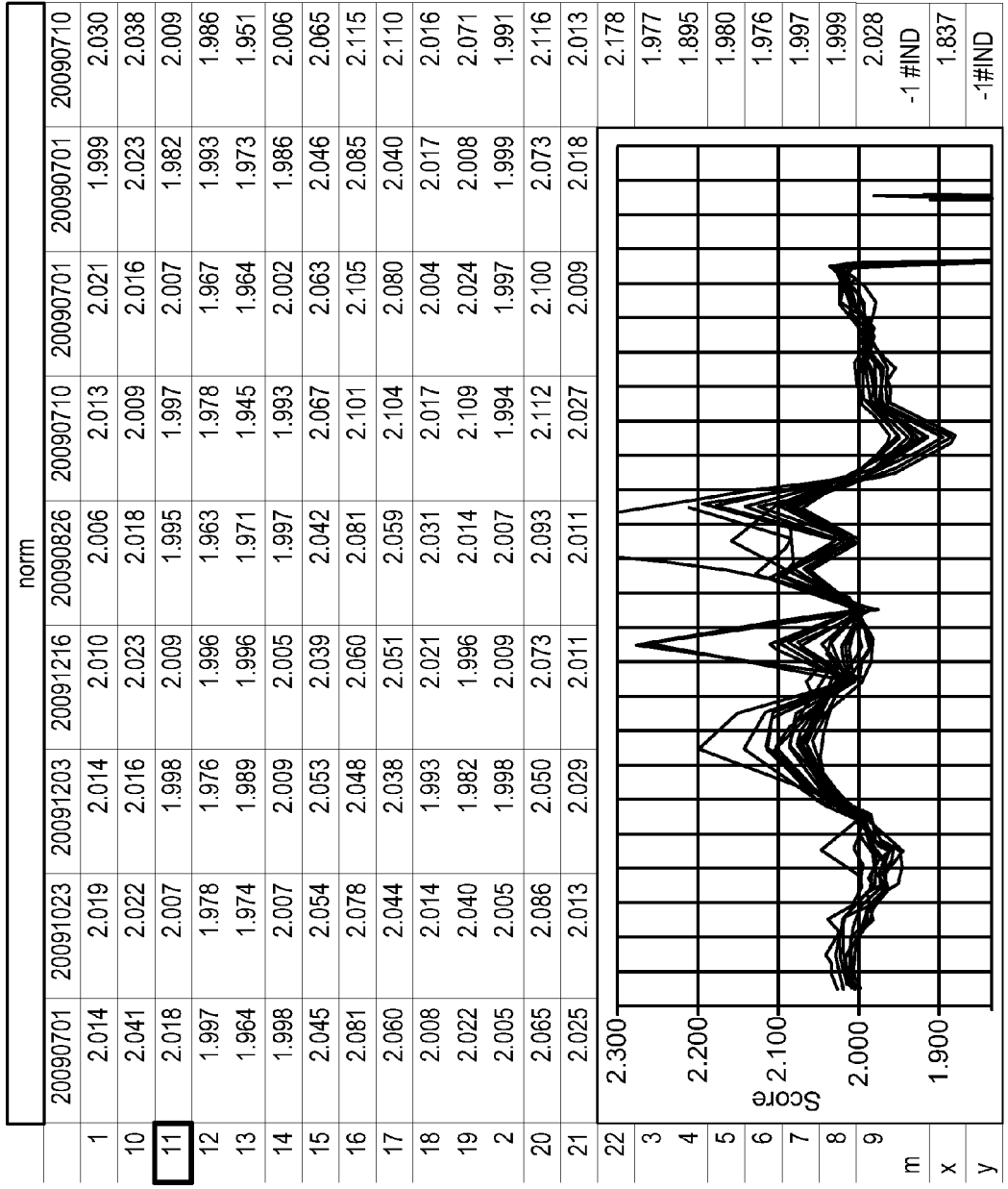
FIG. 6 shows GC normalized abundance score for real maternal blood samples.
Figure 7:
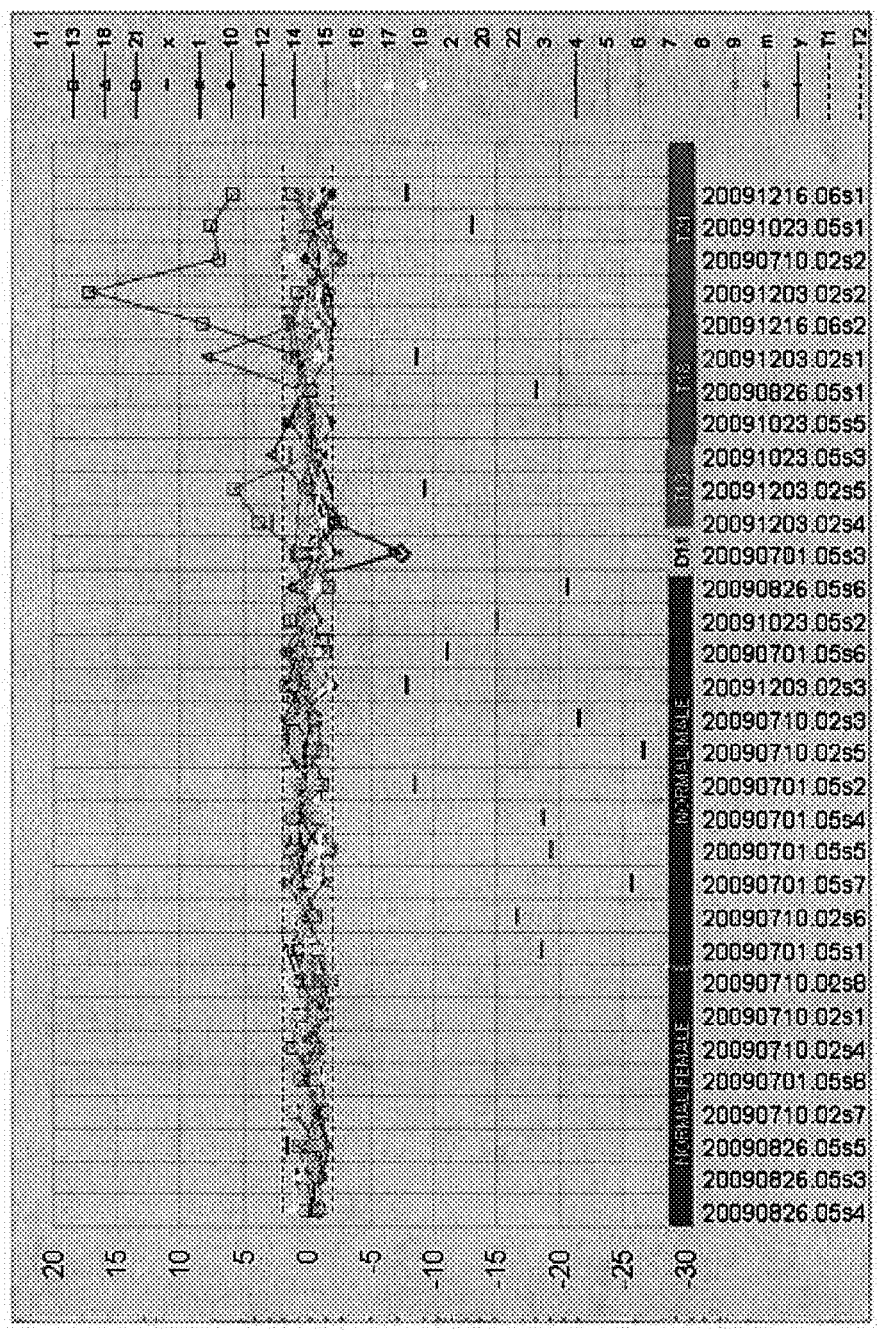
FIG. 7 shows GC normalized z-scores for real maternal blood samples.

FIG. 6, which is discussed in more detail below, presents an example of GC normalized abundance scores for real maternal blood samples, which scores were generated using the above-described method. As can be seen in FIG. 6, the scores for trisomy 18, trisomy 13, and trisomy 21 are notable for their easily detectable separation from the scores for normal cases. Similar results using a modified z-score statistic are depicted in FIG. 7.

Process Context (Examples)

In various embodiments, as explained, the disclosed methods estimate an amount of fetal DNA in the sample, particularly an amount of fetal DNA associated with a sex chromosome or a chromosome associated with an aneuploidy. In various embodiments, the source of sample DNA is blood or other bodily fluid from a pregnant individual. An aneuploidy of the fetus can be detected by comparing actual measured amounts of DNA mapping to a chromosome of interest to estimated amounts of such DNA for the sample. Detecting of more or less than the expected amount of DNA mapped to a particular chromosome can indicate fetal aneuploidy, e.g., detected variations in the amount of DNA mapping to any of human chromosomes 13, 16, 18 or 21. The method can similarly be used to determine a fetus' sex.

A specific example of a method for determining the sex or identifying aneuploidy in a fetus will now be described with reference to FIG. 1A. As shown there, a test 101 begins with isolating DNA from the blood of a pregnant individual. See operation 103. This may be conducted using cell-bound or free DNA. It has been found that free DNA circulating in a mother's blood stream includes about 5 to 10% free DNA from the fetus carried by the mother. Many implementations of the method make use of cell-free DNA. Further, various implementations do not separate maternal DNA and fetal DNA or otherwise distinguish between the two.

After isolating the DNA in operation 103, the process involves reading nucleotide segments (sometimes called tags herein) from this DNA. See operation 105. Typically, this involves reading fixed length sections of DNA, which are the "tags." In some embodiments, this operation makes use of very fast sequencing tools such as massively parallel DNA sequencing tools. In some cases, many thousands or millions of tag sequences are read for a single sample. In specific examples, at least about one million tag sequences are read and mapped, and in more specific examples, at least about five million tag sequences are read and mapped.

Preferably, sequencing is performed in a manner that allows quick and direct assignment of sequenced DNA to particular chromosomes. Generally, there is sufficient information for this purpose in tags of size 30 base pairs or greater. Tags of this size can be unambiguously mapped to single chromosomes. In a specific embodiment, the tag sequences employed in the process are 36 base pairs in length.

Next in the process, the tags are mapped to a chromosome of interest and the number of tags so mapped is determined. See operation 107. This may involve mapping each tag to one of the 23 human chromosomes and determining the number of mapped tags per chromosome. For efficiency, the process need not store or analyze the sequence information from the tags. For example, the process need not identify SNPs in a tag. Rather, operation 107 can simply provide a number of tag sequences that map to a chromosome of interest.

In some embodiments, the method is performed without using a control sample. In other cases, the method provides an internal control which involves determining the number of tags mapping to a control chromosome. For example to detect aneuploidy, counts may be calculated for a both a chromosome suspected of aneuploidy and a chromosome that does not exhibit aneuploidy. A comparison of the calculated counts for these two chromosomes serves as an internal control. In a specific embodiment, one might compare the number of tags mapping to chromosomes 21 and 9, with the mappings to chromosome 9 serving as an internal control for aneuploidy detection in chromosome 21 (e.g., trisomy in chromosome 21).

The depicted process 101 concludes by detecting statistically significant deviations from an expected count or abundance level for the chromosome of interest. See operation 109. In various embodiments of interest, this is done by partitioning the collected sequence data across a source of experimental variability. As explained, one such source is the GC content in the chromosome sequences being mapped. The partitioned data is used to generate an expected tag number that accounts for the experimental variability. The partitioned data may also be employed to provide other characteristics of the data such as an expected variance. By accounting for experimental variability in this manner, the experimental results more accurately reflect deviations from normality in the fetal genome.

It should be noted that the above-described technology is based on a simple blood test and need not even distinguish maternal DNA from fetal DNA. It simply identifies statistically significant aberrations in the amount of DNA associated with different chromosomes in the free DNA circulating in maternal blood. The apparatus and associated software for performing the method quickly generates a tag number associated with one or more of the 23 human chromosomes. This number need not, and preferably does not, distinguish maternal and fetal DNA. When the tag numbers are complete and associated with the individual chromosomes, the relevant process algorithm identifies any statistically significant aberrations in the tag counts. Other than the sex chromosomes, there should be two copies of each human chromosome. In other words, each of the non-sex chromosomes should be diploid. Any deviation from this is a manifestation of aneuploidy.

Figure 1B:
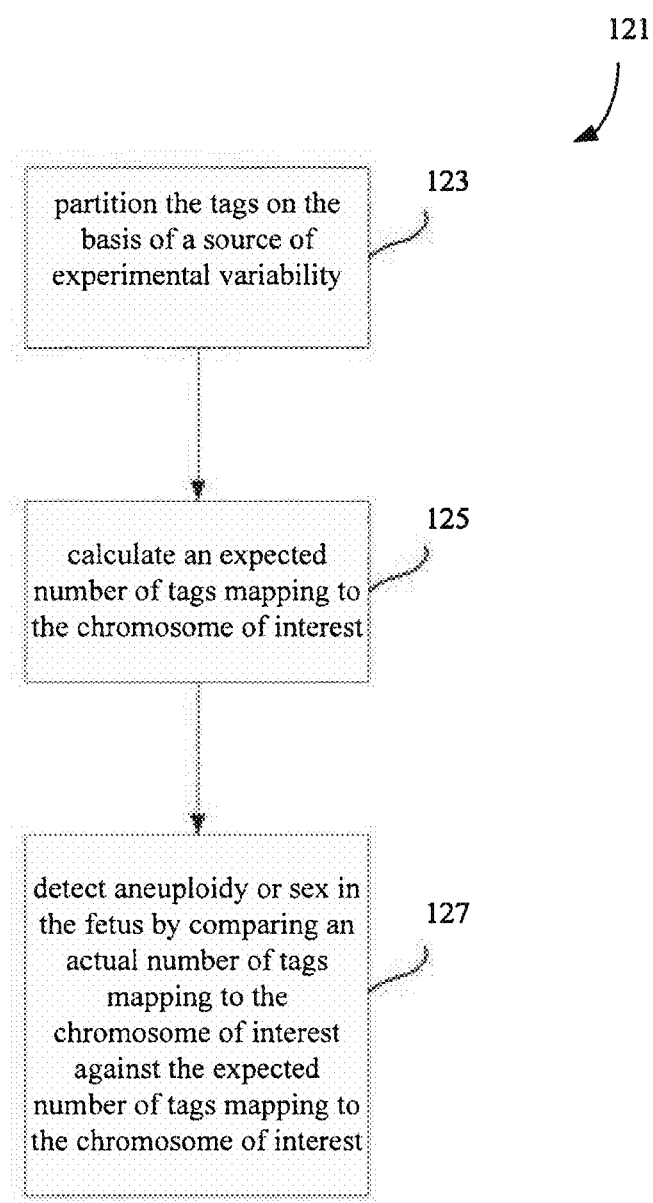
FIG. 1B is a flow chart depicting a generalized method for detecting information about a chromosome by using a partitioning to calculate an expected number of counts mapping to at least one chromosome.

FIG. 1B is a process flow chart depicting an inventive algorithm 121 for implementing operation 109 in FIG. 1A. In the depicted method, the tags mapping the chromosome of interest are first partitioned on the basis of a source of experimental variability (e.g., GC content). See operation 123. Thereafter, an expected number of tags mapping to the chromosome of interest is calculated. See operation 125. This calculation accounts for the experimental variability by using the partitioning. It further includes an assumption about the chromosome of interest (e.g., it assumes that the chromosome exhibits normal ploidy or a sex characteristic). The discussion below presents various examples of this calculation and how partitioning and assumptions about ploidy may be used to generate an expected number of tags. See for example, equation 1 below which provides an expected number E(#R) as a function partitions of generated sequences.

Process 121 concludes by detecting the aneuploidy or sex in the fetus by comparing an actual number of segments mapping to the chromosome of interest against the expected number of segments mapping to the chromosome of interest. See operation 127.

Those of skill in the art will understand that there are alternative statements of the above methods and additionally that there are similar but subtly different methods that accomplish similar results. For example, certain methods for determining a sample trait of a plurality of polynucleotide may be characterized by the following operations: identifying a plurality of polynucleotide sequences within a sample; determining an amount of certain unique sequences within the plurality of polynucleotide sequences identified; normalizing the amount of such identified sequence based on a sequence characteristic (e.g., GC content) that is unique to the unique sequences; and determining the sample trait from the normalized amount of each of the identified sequences. Additionally, certain methods may be characterized as follows: identifying a plurality of polynucleotide sequences within a sample from a subject; assembling each of the plurality of nucleotide sequences into a plurality of bins (e.g., chromosomes) and determining an amount of each bin; normalizing the amount of each bin based on a characteristic that is unique to each bin; and determining a sample trait from the normalized amount of each of the bins.

The sample trait includes without limitation an amount of a particular polynucleotide sequence within a plurality of sequences. The amount can be used to identify, in a quantitative or non-quantitative manner, a sequence such as a gene or a variant thereof. Variants include without limitation an allelic variation or a gene harboring a somatic mutation, such as a mutation linked to a cancer. The sequence can also identify a foreign sequence within the plurality of sequences, e.g., a microorganism such as a virus, bacteria or protozoan within a sample from a host. In some embodiments, the method is used to determine an amplification of a particular sequence, e.g., in the case of cancer. The copy number of a genetic structure, such as a chromosome or a gene, can be determined.

Generally, the methods disclosed herein may be used to diagnose a condition. One focus concerns a modification of conventional techniques employed to determine whether there is an aberrant level of nucleic acid associated with a particular chromosome. As indicated, the methods can be used to determine sex or aneuploidy. In some embodiments, an amount of at least one chromosome is determined, wherein at least one chromosome is human chromosome X, Y, 13, 16, 18 or 21. As described the method can be used to determine fetal sex or aneuploidy by determining the amount of fetal chromosomes in a sample taken directly from a fetus or taken from the maternal subject. In some embodiments, a bodily sample such as blood, plasma or serum from a pregnant individual is used to diagnose a condition of the fetus, e.g., aneuploidy.

In some embodiments, the invention is used to determine the presence of absence of fetal aneuploidy in a maternal plasma specimen containing a mixture of cell free maternal and fetal DNA. The presence of fetal aneuploidy by analysis of plasma cell free DNA can be determined, for example, according to the methods described in U.S. Patent Publication Nos. 2007/0202525 filed Feb. 2, 2007; 2009/0087847 filed Jul. 23, 2008; 2009/0029377 filed Jul. 23, 2008; 2008/0220422 filed Jun. 14, 2007; and 2008/0138809 filed Jun. 14, 2007, all of which are incorporated by reference in their entirety.

An amount of a genomic aberration in the subject can be assessed using the methods of the invention. The genomic aberration can be without limitation a fusion, deletion, insertion, mutation, aberrant methylation or other event. In some embodiments, the subject has been diagnosed with a proliferative disorder. For example, the proliferative disorder can be a cancer. It has been shown that blood plasma and serum DNA from cancer patients contains measurable quantities of tumor DNA, which can be recovered and used as surrogate source of tumor DNA. Tumors are characterized by aneuploidy, or inappropriate numbers of gene sequences or even entire chromosomes. The determination of a difference in the amount of a given sequence i.e. a sequence of interest, in a sample from an individual can thus be used in the diagnosis of a medical condition e.g. cancer.

Embodiments of the invention provide for a method to assess copy number variation of a sequence of interest e.g. a clinically-relevant sequence, in a test sample that comprises a mixture of nucleic acids derived from two different genomes, and which are known or are suspected to differ in the amount of one or more sequence of interest. The mixture of nucleic acids is derived from two or more types of cells. In one embodiment, the mixture of nucleic acids is derived from normal and cancerous cells derived from a subject suffering from a medical condition e.g. cancer.

It is believed that many solid tumors, such as breast cancer, progress from initiation to metastasis through the accumulation of several genetic aberrations. (Sato et al., Cancer Res., 50: 7184-7189 (1990); Jongsma et al., J Clin PAthol: Mol Path 55:305-309 (2002)), each incorporated herein by reference). Such genetic aberrations, as they accumulate, may confer proliferative advantages, genetic instability and the attendant ability to evolve drug resistance rapidly, and enhanced angiogenesis, proteolysis and metastasis. The genetic aberrations may affect either recessive "tumor suppressor genes" or dominantly acting oncogenes. Deletions and recombination leading to loss of heterozygosity (LOH) are believed to play a major role in tumor progression by uncovering mutated tumor suppressor alleles.

Cell free DNA ("cfDNA") has been found in the circulation of patients diagnosed with malignancies including but not limited to lung cancer (Pathak et al. Clin Chem 52:1833-1842 (2006)), prostate cancer (Schwartzenbach et al. Clin Cancer Res 15:1032-8 (2009)), and breast cancer (Schwartzenbach et al. available online at breast-cancer-research.com/content/11/5/R71 (2009)). Identification of genomic instabilities associated with cancers that can be determined in the circulating cfDNA in cancer patients is a potential diagnostic and prognostic tool. In one embodiment, the method of the invention assesses copy number variation ("CNV") of a sequence of interest in a sample comprising a mixture of nucleic acids derived from a subject that is suspected or is known to have cancer e.g. carcinoma, sarcoma, lymphoma, leukemia, germ cell tumors and blastoma. In one embodiment, the sample is a plasma sample derived from peripheral blood and that comprises a mixture of cfDNA derived from normal and cancerous cells. In another embodiment, the biological sample that is needed to determine whether a CNV is present is derived from a mixture of cancerous and non-cancerous cells from other biological fluids including but not limited to serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples, or in tissue biopsies, swabs or smears.

The sequence of interest is a nucleic acid sequence that is known or is suspected to play a role in the development and/or progression of the cancer. Examples of a sequence of interest include nucleic acids sequences that are amplified or deleted in cancerous cells as described in the following.

Dominantly acting genes associated with human solid tumors typically exert their effect by overexpression or altered expression. Gene amplification is a common mechanism leading to upregulation of gene expression. Evidence from cytogenetic studies indicates that significant amplification occurs in over 50% of human breast cancers. Most notably, the amplification of the proto-oncogene human epidermal growth factor receptor 2 (HER2) located on chromosome 17 (17q21-q22)), results in overexpression of HER2 receptors on the cell surface leading to excessive and dysregulated signaling in breast cancer and other malignancies (Park et al., Clinical Breast Cancer 8:392-401 (2008) incorporated herein by reference). A variety of oncogenes have been found to be amplified in other human malignancies.

Examples of the amplification of cellular oncogenes in human tumors include amplifications of: c-myc in promyelocytic leukemia cell line HL60, and in small-cell lung carcinoma cell lines, N-myc in primary neuroblastomas (stages III and IV), neuroblastoma cell lines, retinoblastoma cell line and primary tumors, and small-cell lung carcinoma lines and tumors, L-myc in small-cell lung carcinoma cell lines and tumors, c-myb in acute myeloid leukemia and in colon carcinoma cell lines, c-erbb in epidermoid carcinoma cell, and primary gliomas, c-K-ras-2 in primary carcinomas of lung, colon, bladder, and rectum, N-ras in mammary carcinoma cell line (Varmus H., Ann Rev Genetics 18: 553-612 (1984) (cited in Watson et al., Molecular Biology of the Gene (4th ed.; Benjamin/Cummings Publishing Co. 1987), each incorporated herein by reference).

Chromosomal deletions involving tumor suppressor genes may play an important role in the development and progression of solid tumors. The retinoblastoma tumor suppressor gene (Rb-1), located in chromosome $13_814$, is the most extensively characterized tumor suppressor gene. The Rb-1 gene product, a 105 kDa nuclear phosphoprotein, apparently plays an important role in cell cycle regulation (Howe et al., Proc Natl Acad Sci (USA) 87:5883-5887 (1990), incorporated herein by reference). Altered or lost expression of the Rb protein is caused by inactivation of both gene alleles either through a point mutation or a chromosomal deletion. Rb-i gene alterations have been found to be present not only in retinoblastomas but also in other malignancies such as osteosarcomas, small cell lung cancer (Rygaard et al., Cancer Res 50: 5312-5317 (1990)), incorporated herein by reference) and breast cancer. Restriction fragment length polymorphism (RFLP) studies have indicated that such tumor types have frequently lost heterozygosity at 13q suggesting that one of the Rb-1 gene alleles has been lost due to a gross chromosomal deletion (Bowcock et al., Am J Hum Genet, 46: 12 (1990), incorporated herein by reference). Chromosome 1 abnormalities including duplications, deletions and unbalanced translocations involving chromosome 6 and other partner chromosomes indicate that regions of chromosome 1, in particular 1q21-1q32 and 1p11-13, might harbor oncogenes or tumor suppressor genes that are pathogenetically relevant to both chronic and advanced phases of myeloproliferative neoplasms (Caramazza et al., Eur J Hematol 184:191-200 (2010), incorporated herein by reference). Myeloproliferative neoplasms are also associated with deletions of chromosome 5. Complete loss or interstitial deletions of chromosome 5 are the most common karyotypic abnormality in myelodysplastic syndromes (MDSs). Isolated del(5q)/5q-MDS patients have a more favorable prognosis than those with additional karyotypic defects, who tend to develop myeloproliferative neoplasms (MPNs) and acute myeloid leukemia. The frequency of unbalanced chromosome 5 deletions has led to the idea that 5q harbors one or more tumor-suppressor genes that have fundamental roles in the growth control of hematopoietic stem/progenitor cells (HSCs/HPCs). Cytogenetic mapping of commonly deleted regions (CDRs) centered on 5q31 and 5q32 identified candidate tumor-suppressor genes, including the ribosomal subunit RPS14, the transcription factor Egr1/Krox20 and the cytoskeletal remodeling protein, alpha-catenin (Eisenmann et al., Oncogene 28:3429-3441 (2009), each incorporated herein by reference). Cytogenetic and allelotyping studies of fresh tumours and tumour cell lines have shown that allelic loss from several distinct regions on chromosome 3p, including 3p25, 3p21-22, 3p21.3, 3p12-13 and 3p14, are the earliest and most frequent genomic abnormalities involved in a wide spectrum of major epithelial cancers of lung, breast, kidney, head and neck, ovary, cervix, colon, pancreas, esophagus, bladder and other organs. Several tumor suppressor genes have been mapped to the chromosome 3p region, and are thought that interstitial deletions or promoter hypermethylation precede the loss of the 3p or the entire chromosome 3 in the development of carcinomas (Angeloni D., Briefings Functional Genomics 6:19-39 (2007), incorporated herein by reference).

Newborns and children with Down syndrome (DS) often present with congenital transient leukemia and have an increased risk of acute myeloid leukemia and acute lymphoblastic leukemia. Chromosome 21, harboring about 300 genes, may be involved in numerous structural aberrations, e.g., translocations, deletions, and amplifications, in leukemias, lymphomas, and solid tumors. Moreover, genes located on chromosome 21 have been identified that play an important role in tumorigenesis. Somatic numerical as well as structural chromosome 21 aberrations are associated with leukemias, and specific genes including RUNX1, TMPRSS2, and TFF, which are located in 21q, play a role in tumorigenesis (Fonatsch C Gene Chromosomes Cancer 49:497-508 (2010), incorporated herein by reference).

In one embodiment, some of the methods described herein provide a means to assess the association between gene amplification and the extent of tumor evolution. Correlation between amplification and/or deletion and stage or grade of a cancer may be prognostically important because such information may contribute to the definition of a genetically based tumor grade that would better predict the future course of disease with more advanced tumors having the worst prognosis. In addition, information about early amplification and/or deletion events may be useful in associating those events as predictors of subsequent disease progression. Gene amplification and deletions as identified by methods disclosed herein can be associated with other known parameters such as tumor grade, histology, Brd/Urd labeling index, hormonal status, nodal involvement, tumor size, survival duration and other tumor properties available from epidemiological and biostatistical studies. For example, tumor DNA to be tested by these methods could include atypical hyperplasia, ductal carcinoma in situ, stage I-III cancer and metastatic lymph nodes in order to permit the identification of associations between amplifications and deletions and stage. The associations made may make possible effective therapeutic intervention. For example, consistently amplified regions may contain an overexpressed gene, the product of which may be able to be attacked therapeutically (for example, the growth factor receptor tyrosine kinase, p185$^{HER2}$).

The methods can be used to identify amplification and/or deletion events that are associated with drug resistance by determining the copy number variation of nucleic acids from primary cancers to those of cells that have metastasized to other sites. If gene amplification and/or deletion is a manifestation of karyotypic instability that allows rapid development of drug resistance, more amplification and/or deletion in primary tumors from chemoresistant patients than in tumors in chemosensitive patients would be expected. For example, if amplification of specific genes is responsible for the development of drug resistance, regions surrounding those genes would be expected to be amplified consistently in tumor cells from pleural effusions of chemoresistant patients but not in the primary tumors. Discovery of associations between gene amplification and/or deletion and the development of drug resistance may allow the identification of patients that will or will not benefit from adjuvant therapy. (See pending U.S. patent application Ser. Nos. 12/958,352 filed Dec. 1, 2010, and 12/958,353 filed Dec. 1, 2010, incorporated herein by reference).

Thus, in general, the aberration under consideration can be causative or only indicative of the proliferative disorder. In some embodiments, the sample comprises or is suspected to comprise tumor cells. In some embodiments, the sample is bodily fluid, e.g., blood. In an exemplary embodiment, the methods of the invention are used to determine an amount of tumor DNA circulating in the blood of a subject diagnosed with a proliferative disorder. In some embodiments, the suspect is suspected but not confirmed to have the disorder. The methods can be used in the diagnosis of the disorder.

In some embodiments, the variance of the detection of specific sequences or bins of sequences, e.g., corresponding to a chromosome, is less than about 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or less than about 0.1%.

In an aspect, the invention provides a method for determining fetal aneuploidy from a maternal blood sample. The method comprises normalizing a plurality of polynucleotide sequences reads from the sample and making the determination based on the sequence reads, wherein the method has a precision of at least 60%, 65%, 70%, 75%, 80%, 85%, 90%, 91%, 92%, 93%, 94%, 95%, 96%, 97%, 98%, or at least 99%. In embodiments, the method uses the methodology provided herein to determine a normalized amount of a fetal polynucleotide found within a maternal blood sample. The amounts of the fetal chromosomes can be used to determine fetal aneuploidy.

In an aspect, the invention provides a method for determining fetal aneuploidy from a maternal sample, the method comprising comparing the distribution of a plurality of polynucleotide sequences reads from a sample with an expected distribution based on estimated fetal DNA concentration in the maternal sample. In embodiments, the method has a precision of at least 60%, 65%, 70%, 75%, 80%, 85%, 90%, 91%, 92%, 93%, 94%, 95%, 96%, 97%, 98%, or at least 99%. In embodiments, the method uses the methodology provided herein to determine a normalized amount of a fetal polynucleotide found within a maternal blood sample. The amounts of the fetal chromosomes can be compared to the expected amounts to determine fetal aneuploidy. The expected amounts may include without limitation the amounts of fetal DNA expected if the fetus is male or female, or if the fetus has or does not have an aneuploidy or other chromosomal abnormality. The present methods are applicable to any method that is used for determining fetal aneuploidies e.g. Fan et al., PNAS 105:16266-16271 [2008]; Chiu et al. PNAS 105: 20458-20463 [2008]; Chiu et al., BMJ 2011; 342:c7401 [2011]; US Patent Publication Nos. 2007/0202525 filed Feb. 2, 2007, 2010/0138165 filed Jan. 29, 2010, 2009/0029377 filed Jul. 23, 2008, 2010/0112590 filed Nov. 6, 2009, and pending U.S. patent application Ser. Nos. 12/958,352 filed Dec. 1, 2010 and 12/958,353 filed Dec. 1, 2010, each incorporated herein by reference.

Implementation Options

As should be clear from the above discussion, the condition to be detected need not be aneuploidy in a fetus nor does the sample being analyzed need to be DNA taken from the blood of a pregnant female. The following discussion provides some indication of the range of subjects, samples, and sequencing methods that may be used with the disclosed techniques for accounting for experimental variation.

The subject providing a sample to be tested can be an organism comprising polynucleotide sequences, e.g., a plant, an insect such as a fly, or an animal. In some embodiments, the subject is a mammal, e.g., a mouse, rat, dog, monkey or human. The subject can be a pregnant individual. The subject might be an individual with a disease such as a cancer, or might be infected with a foreign body such as a microorganism, e.g., a virus. The sample can comprise a bodily fluid from the subject, e.g., blood, plasma, serum, sputum, saliva, urine, excrement, pus, lymph, mucous or the like. For example, the subject can be pregnant and the sample can be a plasma sample.

In various embodiments, the sample includes polynucleotide sequences (such as the above described tags) which are detected by assaying. The polynucleotide sequences can be deoxyribonucleic acid (DNA) polynucleotide sequences, both naturally occurring and/or synthetic sequences. In other embodiments, the polynucleotide sequences comprise ribonucleic acid (RNA), e.g., mRNA, tRNA, siRNA, small RNAs, micro RNAs or the like. The sequences may have non-naturally occurring nucleic acid building blocks, e.g., nucleotides that have chemical modifications not typically found in nature. Nucleotides include without limitation pyrimidines comprising cytosine (C), thymine (T), and uracil (U), and purines comprising adenine (A) and guanine (G).

In some embodiments, the plurality of polynucleotide sequences comprise isoforms of genes. Using the method, a particular allelic or genetic mutation can be identified. In some embodiments, the plurality of polynucleotide sequences comprises genomic DNA.

In some embodiments, the sample is a maternal plasma sample comprising a mixture of maternal and fetal cell free DNA. The methods may involve sequencing of the cell free DNA; mapping the sequence reads to chromosomes; normalizing the data of mapped chromosome reads based on GC content; and determining the presence or absence of fetal aneuploidy according to the normalized data.

In some embodiments, the methods further employ PCR or a related technique for amplifying the plurality of nucleotide sequences before identifying or mapping them.

In one embodiment, the method described herein employs next generation sequencing technology (NGS) in which clonally amplified DNA templates or single DNA molecules are sequenced in a massively parallel fashion within a flow cell (e.g. as described in Volkerding et al. Clin Chem 55:641-658 [2009]; Metzker M Nature Rev 11:31-46 [2010]). In addition to high-throughput sequence information, NGS provides digital quantitative information, in that each sequence read is a countable "sequence tag" representing an individual clonal DNA template or a single DNA molecule. The sequencing technologies of NGS include pyrosequencing, sequencing-by-synthesis with reversible dye terminators, sequencing by oligonucleotide probe ligation and real time sequencing.

Some of the sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies are encompassed by the disclosed method and include the SMRT™ technology of Pacific Biosciences, the Ion Torrent™ technology, and nanopore sequencing being developed for example, by Oxford Nanopore Technologies.

While the automated Sanger method is considered as a 'first generation' technology, Sanger sequencing including the automated Sanger sequencing, can also be employed by the disclosed method. Additional sequencing methods that comprise the use of developing nucleic acid imaging technologies e.g. atomic force microscopy (AFM) or transmission electron microscopy (TEM), are also encompassed by the disclosed method. Exemplary sequencing technologies are described below.

In one embodiment, the DNA sequencing technology that is used in the disclosed methods is the Helicos True Single Molecule Sequencing (tSMS) (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes PCR-based amplification in the preparation of the sequencing libraries, and the directness of sample preparation allows for direct measurement of the sample, rather than measurement of copies of that sample.

In one embodiment, the DNA sequencing technology that is used in the disclosed methods is the 454 sequencing (Roche) (e.g. as described in Margulies, M. et al. Nature 437:376-380 (2005)). 454 sequencing involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed.

In one embodiment, the DNA sequencing technology that is used in the disclosed methods is the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In one embodiment, the DNA sequencing technology that is used in the disclosed methods is the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength identifiers (ZMW identifiers) that obtain sequence information while phospolinked nucleotides are being incorporated into the growing primer strand. A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Identification of the corresponding fluorescence of the dye indicates which base was incorporated. The process is repeated.

In one embodiment, the DNA sequencing technology that is used in the disclosed methods is nanopore sequencing (e.g. as described in Soni GV and Meller A. Clin Chem 53: 1996-2001 [2007]). Nanopore sequencing DNA analysis techniques are being industrially developed by a number of companies, including Oxford Nanopore Technologies (Oxford, United Kingdom). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence.

In one embodiment, the DNA sequencing technology that is used in the disclosed methods is the chemical-sensitive field effect transistor (chemFET) array (e.g., as described in U.S. Patent Publication No. 2009/0026082 filed Dec. 17, 2007). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In one embodiment, the DNA sequencing technology that is used in the disclosed methods is the Halcyon Molecular's method that uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In one embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be identified by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct identification allows recordation of nucleotide incorporation in seconds.

Other sequencing methods include digital PCR and sequencing by hybridization. Digital polymerase chain reaction (digital PCR or dPCR) can be used to directly identify and quantify nucleic acids in a sample. Digital PCR can be performed in an emulsion. Individual nucleic acids are separated, e.g., in a microfluidic chamber device, and each nucleic can is individually amplified by PCR. Nucleic acids can be separated such there is an average of approximately 0.5 nucleic acids/well, or not more than one nucleic acid/well. Different probes can be used to distinguish fetal alleles and maternal alleles. Alleles can be enumerated to determine copy number. In sequencing by hybridization, the hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be identified and used to identify the plurality of polynucleotide sequences within the sample.

In one embodiment, the method employs massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA e.g. cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments of <300 bp, and maternal cfDNA has been estimated to circulate as fragments of between about 0.5 and 1 Kb (Li et al., Clin Chem, 50: 1002-1011 (2004)). Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. In one embodiment, the randomly fragmented genomic DNA e.g. cfDNA, is amplified using PCR before it is subjected to cluster amplification. Alternatively, an amplification-free genomic library preparation is used, and the randomly fragmented genomic DNA e.g. cfDNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence identification is achieved using laser excitation and total internal reflection optics. Short sequence reads of about 20-40 bp e.g. 36 bp, are aligned against a repeat-masked reference genome and genetic differences are called using specially developed data analysis pipeline software. After completion of the first read, the templates can be regenerated in situ to enable a second read from the opposite end of the fragments. Thus, either single-end or paired end sequencing of the DNA fragments is used according to the method. Partial sequencing of DNA fragments present in the sample is performed, and sequence tags comprising reads of predetermined length e.g. 36 bp, that are mapped to a known reference genome are counted.

The length of the sequence read is associated with the particular sequencing technology. NGS methods provide sequence reads that vary in size from tens to hundreds of base pairs. In some embodiments of the method described herein, the sequence reads are about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the sequence reads are 36 bp. Other sequencing methods that can be employed by the disclosed methods include the single molecule sequencing methods that can sequence nucleic acids molecules >5000 bp. The massive quantity of sequence output is transferred by an analysis pipeline that transforms primary imaging output from the sequencer into strings of bases. A package of integrated algorithms performs the core primary data transformation steps: image analysis, intensity scoring, base calling, and alignment.

As indicated, various disclosed methods include mapping some or all of a generated plurality of nucleotide sequences into a plurality of "bins" and determining an amount of sequences in one or more bins. For example, the identity of the plurality of sequences within the sample is identified, and based on their identification, the sequences can then be grouped together into a "bin." This operation allows the individual sequences to be used to identify an amount of a larger sequence. For example, the bins may be without limitation chromosomes, viral genomes, genes, gene fragments, exons or introns.

The method can be used to identify, e.g., more than 2, 3, 4, 5, 6, 7, 8, 9, 10, 15, 20, 25, 30, 40, 50, 60, 70, 80, 90, 100, 200, 300, 400, 500, 600, 700, 800, 900, 1000, 5,000, 10,000, 25,000, 50,000 100,000, 250,000, 500,000, 1,000,000, 2,500,000, 5,000,000, 10,000,000, 25,000,000, 50,000,000, 100,000,000 or more individual sequences. These individual sequences can then be mapped to bins, e.g., chromosomes, so that a sample trait is that of a chromosome.

A "count" of one or more chromosomes can be determined. An amount of a chromosome can be determined using the normalized amount or number of the identified polynucleotide sequences (or tags). In some embodiments, the plurality of polynucleotide sequences identified by the methods is from at least one chromosome suspected of aneuploidy. In some embodiments, the plurality of polynucleotide sequences are from at least one chromosome that is not suspected of aneuploidy and at least one chromosome suspected of aneuploidy. Thereby, the method can be used to determine an aneuploidy, or an aberrant chromosomal copy number.

In a typical embodiment, the method generates a read and directly maps the read tag to a chromosome. One need not generate a sequence in a conventional sense. In fact, one need not distinguish maternal from fetal chromosomes. It is sufficient to simply count the number of tags mapped to a chromosome under consideration. For a sample containing 5 to 10% fetal DNA, an increase or decrease of about 1-5% in the quantity of DNA in any chromosome indicates an aberration in the fetal genome.

Various computational methods can be used to map each identified sequence to a bin, e.g., by identifying all sequences in the sample that map to a particular gene, chromosome, or other structure. A number of computer algorithms exist to align sequences, including without limitation BLAST (Altschul et al., 1990), BLITZ (MPsrch) (Sturrock & Collins, 1993), and FASTA (Person & Lipman, 1988) or variations thereof. In some embodiments, the sequences of the bins are found in nucleic acid databases known to those in the art, including without limitation GenBank, dbEST, dbSTS, EMBL (the European Molecular Biology Laboratory), and the DDBJ (the DNA Databank of Japan). BLAST or similar tools can be used to search the identified sequences against the sequence databases, and search hits can be used to sort the identified sequences into the appropriate bins.

Calculations Employing Partition Methods

Certain disclosed techniques for calculating an expected number of segments mapping to a region of interest can be represented mathematically as discussed in this section. Similarly certain disclosed techniques for determining a trait of interest (e.g., aneuploidy) can be represented mathematically. To assist this description, certain terms may understood to have the following meanings A "mapping" is a process performed on two sequences or strings such as a generated tag sequence and a substring in genome. The mapping of two sequences or strings may be viewed as an alignment or matching such that identical bases are maximized. For example, if d maps to R, then d aligns with a w length subset of R. For notational convenience, it may be assumed that each generated sequence has at most one mapping. As discussed above, one example of mapping involves aligning through BLAST or other suitable tool 36 bp tags to specific chromosomes.

w is a fixed word size. In one example, it is the size of a tag read via a sequencing process such as one of the above-described sequencing techniques. In a specific example, w is 36 base pairs.

G is a genome containing length w substrings $\{g_1, \ldots, g_m\}$. The human genome has approximately three billion such substrings, for small lengths w.

D is the set of length w substrings that map to G (e.g., D is approximately $3 \times 10^9 - w$ for the human genome).

R is a region within a genome G. It is a continuous subset of base pairs of G, which may for example contain base pairs from only one chromosome. In a specific example, R is the entire string of base pairs in chromosome 21.

R is number of generated sequences that map to R. This is a subset of the experimentally generated length w fragments that map to R. In a specific example, these could be the sequences that map to chromosome 21.

Len(R)—This is the number of w length substrings in a region R. These can be understood by taking a w length substring window at one end of R and moving it one base at a time toward the other end of R. Each position of the window will produce a new substring. The total number of such substrings in R is equal to the number of bases in R minus length w and plus 1 (R=# of bases in R−w+1).

P(R) is a partition of length w substrings or region R. A partition, P, of a set is an assignment of elements of R to subsets (partition levels) such that each element of R is in one and only one subset.

An example of a partition might be the generated sequences that have a GC content of 55%. All expected and generated sequences having this GC content.

$n_i$ is the number of actually generated sequences (e.g., 36mers) having the property specified by the partition under consideration (e.g., a GC content of 55%). Note that $n_i$ will be a fraction of the total number of actually generated sequences.

$|R_i|$ is the number of length w substrings within R assigned to partition level i. This is typically known or derived from pre-existing information (e.g., the human genome sequence). A particular fraction of the substrings within R fall within this partition.

$\#R_i$ is the number of actually generated sequences in an experiment that map to R and belong to partition level i. (e.g., the generated sequences that map to R (chromosome 21) and have a GC content of 55%.)

Copy number estimates and tests for aberration for an analyte, chromosomal region, or set, R, can be defined from moments of #R, the number of generated sequences mapping to R. Given a partition P of the w-words of genome G, n generated sequences, and assuming that the number of generated sequences at partition level i in region R follows a Binomial distribution, one can calculate the expected number of sequences matching R (the first moment). Assuming uniformity, Equation 1-Expected number of counts for a region $$\#R_i \sim \text{Binomial}(n, \text{Bernoulli } prob) = \text{Binomial}\left(n_i, \frac{|R_i|}{|G_i|}\right), \text{ and}$$

$$E(\#R) = \sum_{\forall i \in P(G)} E(\#R_i) = \sum_{\forall i \in P(G)} \frac{n_i |R_i|}{|G_i|}$$

Note that this expected number is calculated using test data; $n_i$ is known only after collecting the test data. Note however that $|R_i|$ and $|G_i|$ will be known without resort to the test data. By partitioning across a source of experimental variability (that is wholly or substantially unrelated to the condition to be detected), the expected number accounts for this variability. In other words, the partitioning can capture at least one source of inter-experimental variation and as a consequence account for the bias created by this variation to give a more accurate reading of the test results. As explained above, sequence length and GC content are the two sources of experimental variability identified in the disclosure.

Implicit in equation 1 is the assumption that the test DNA has a particular ratio of DNA between the region of interest (e.g., chromosome 21) and the entire genome. This ratio is reflected in equation $|R_i|/|G_i|$. In a test to identify trisomy in chromosome 21, this ratio is calculated using the assumption that there are two, and not three, copies of chromosome 21.

Assuming independence of the $\#R_i$, the variance of #R (the second moment) can also be expressed as the following summation:

$$\text{Var}(\#R) = \sum_{\forall i \in P(G)} \text{Var}(\#R_i) = \sum_{\forall i \in P(G)} \left[\frac{n_i |R_i|}{|G_i|}\left(1 - \frac{|R_i|}{|G_i|}\right)\right] \quad \text{Equation 2}$$

Similar to Equation 1, Equation 2 make use of test data (i.e., both use a partitioned value of the generated sequences, $n_i$). But rather than providing an expected mean (first moment), it provides an expected variance in the generated segments (second moment).

Considering a region R (e.g., chromosome 21) and a partition level i (e.g., GC content of 55%), each term of Equation 1 (and Equation 2) indicates how many generated sequences in partition level i one should expect to map to R (and what is the statistical distribution of those mapped sequences). For example, if partition level i contains all sequences having a GC content of 55%, and there are 100 length w sequences having GC content of 55% in chromosome 21 and there are 200 total length w sequences having GC content of 55% in the entire genome, then one would expect that one half of your generated sequences in the 55% GC partition level will map to chromosome 21.

Given the selected partition function and moment estimators one can define dose, abundance, or copy number estimates. For example, aberrations in a trait under test can be detected by comparing the actual number of generated sequences mapping to a region (#R) to the expected number of such sequences (E(#R)). Such comparison may include, e.g., a difference or quotient of these numbers. In some embodiments, the comparisons take the form of an estimated copy number. Generally, the copy number represents the number of copies of region R in the sample being tested. For human diagnostic applications autosomal nominal copy number is two. Human male sex chromosome nominal copy number is one in normal cases. Using a difference or quotient of actual generated and estimated tag numbers, one can detect a significant deviation from the nominal copy number.

There are several ways copy number estimates can be constructed from expected word counts. For example Equation 3-Linear scaling copy number estimate for a region $$CN_1(R, D, P, G) = \text{Nominal Copy Number} + \frac{(\#R - E\#R)}{\text{scale}}$$

Equation 4-Ratio copy number estimate $$CN_2(R, D, P, G) = \frac{(\text{Nominal Copy Number})\#R}{E\#R}$$

or

The family of copy number estimates includes Equations 3 and 4 and numerous variants thereof. Many variations and transformations lead to alternate copy number formulas which are known to those of skill in the art and intended to be covered. Equations 3 and 4 are centered on a nominal copy number (e.g., 2 for diploid chromosomes), but this need not be the case.

In many cases detection of aberration is at least as important as actually estimating a region copy number within a sample. In some cases, a value similar to a z-score can be determined for each region.

$$Z(R, D, P, G) = \frac{\#R - (\text{normal case } \# R \text{ center})}{(\text{normal case } \# R \text{ std dev})} \approx \frac{\# R - E(\#R)}{\sqrt{\text{Var}(\#R)}} \quad \text{Equation 5}$$

If E(#R) from Equation 1 and Variance from Equation 2 perform well, then Z~Φ (the standard normal distribution) and standard methods can be used with appropriate multiple testing correction to define confidence intervals for counts of generated sequences matching regions present at nominal copy number. Note that Equation 5 employs a comparison of the expected number and the actual counted number of tags (a difference) to facilitate identification of aberrations in the region of interest R. The z-score equation scales this difference by the expected standard deviation value (which is the square root of variance from Equation 2).

Various embodiments allow for controlling fixed bias in the method using trained parameters. A variety of factors can introduce bias into Equation 1 and Equation 2 as a predictor of #R behavior thus making the distribution of Z above not standard normal. Fortunately, for some choices of partition and copy number formula, E(#R) captures most inter-experimental variation and bias appears to be constant in real data. In this case the limited use of normal case trained parameters can turn Equation 5 into a precise tool for the detection of aberration.

Given a set, S={s1, . . . , sn} S={$s_1$, . . . , $s_s$} of samples with no aberration, one may estimate the center and spread of copy number, CNj(R,si,P,G), for all $s_i$ in S. In the case of aneuploidy detection, samples with no aberration may be taken from pregnant individuals carrying genetically normal fetuses (fetuses without aneuploidy). Using the resulting "trained" values of mean and variance (as defined in equation 6), one can obtain a modified z-statistic score using equation 7 and copy number estimate (CN calculated using equations 3 or 4).

For example, for each region of interest R, one may estimate the following parameters:

$$\text{center } \Delta_R = \frac{1}{n} \sum_{s_i \in S} CN_j(R, s_i, P, G) \quad \text{Equation 6}$$
$$= \text{sample mean of } CN(S)$$
$$\text{spread } \Gamma_R = \sqrt{\text{sample veriance of } CN(S)}$$

One may alternately use (n−1) in Equation 6 denominator terms.

A modified Z statistic using the trained parameters may be defined as follows:

Equation 7 Modified Z statistic $$Z_R = \frac{CN_j(R) - \Delta_R}{\Gamma_R}$$

Z is normally distributed with a mean of zero and a variance of one when the trained parameters reflect the data, D, being studied.

One basic application of the copy number expression in Equation 4 will now be described. Setting the partition of G to be <base index>+<chromosome number> defines the identity partition, I, which puts every genome w-tuple sequence in its own partition bin. Setting autosome nominal copy number to 2 and using the "ratio" copy number formula from Equation 4 one may define the following length normalized score:

$$\text{Length Normalized Score} = CN_1(R, D, I, G) \quad \text{Equation 8}$$
$$= 2 \frac{len(G) \cdot \#R}{Len(R) \cdot n}$$

For example the copy number estimate for chromosome 21 is $$\frac{2 len(G) \#R}{len(R) n}.$$

A GC normalized score may be obtained by setting the partition, $P_{GC}$, to be the GC count (or the GC percentage) of each length w substring. Using Equation 1 (expected number of tags mapping to region R), and summing over all possible GC concentrations in a w-length sequence (e.g., from 0-36) gives the following:

$$E(\#R) = \sum_{\forall i \in P(G)} \frac{n_i |R_i|}{|G_i|} \quad \text{Equation 9}$$
$$= \sum_{i=1}^{w+1}$$

-continued $$\frac{(\text{\# genertated } seqs \text{ with } GC \text{ count } i)}{(num. \text{ length } w \text{ substrings in } G \text{ with } GC \text{ count } i)}$$
$$(\text{\# } len. \; w \text{ substrings in } R \text{ of } GC \text{ count } i)$$

Using the copy number function from Equation 3, one may define a copy number estimate as follows:

$$GC \text{ Normalized Score} = 2 + \left[ \#R - \sum_{i=1}^{w} \frac{|R_i| n_i}{|G_i|} \right] \quad \text{Equation 10}$$

Studies on maternal blood samples have shown that, even without transformation into a modified Z-score, the GC normalization of Equation 10 provides excellent discrimination between normal and aneuploidy cases (FIG. 6).

The melting temperature (free energy) of the tag sequences can also be employed to normalize the score. Setting the partition, $P_{\Delta G}$, to be dg=⌊100*ΔG⌋ with delta G as described in equation 2 of SantaLucia (1998, SantaLucia J, "A Unified View of Polymer, Dumbbell, and Oligonucleotide DNA Nearest-Neighbor Thermodynamics", PNAS USA, v 95, pp. 1460-1465) incorporated herein by reference.

$$E(\#R) = \sum_{i=min(dg)}^{max(dg)} \frac{|R_i| Len(R)}{|G_i|} \quad \text{Equation 11}$$

and

Melting Temp Normalized Score =

$$2 + \left[ \#R - \sum \frac{|R_i| Len(R)}{|G_i|} \right]$$

Exemplary computer code to calculate delta G is shown here.

```
Procedure : dGCalc
'Author   : jburke
'Purpose  : Definition of partition function for removing inter-batch effect
in chromosomal aberration detection
'-------------------------------------------------------------------------
'
Public Function dGCalc(s1 As String)
    Dim SeqLen As Long
    Dim i As Long
    Dim base As String
    Dim d1 As Double
    On Error GoTo dGCalc__Error
    SeqLen = Len(s1)
    d1 = 0
    s1 = StrConv(s1, vbLowerCase)
    base = Mid(s1, 1, 1)
    If base = "a" Or base = "t" Then
        d1 = d1 + 0.98
    Else
        d1 = d1 + 1.03
    End If
    For i = 1 To SeqLen − 1
        base = Mid(s1, i, 2)
        If base = "aa" Or base = "tt" Then
            d1 = d1 − 1
        ElseIf base = "at" Then
            d1 = d1 − 0.88
        ElseIf base = "at" Or base = "ta" Then
            d1 = d1 − 0.58
        ElseIf base = "ta" Then
            d1 = d1 − 1.45
```

-continued

```
        ElseIf base = "ca" Or base = "tg" Then
            d1 = d1 - 1.44
        ElseIf base = "gt" Or base = "ac" Then
            d1 = d1 - 1.28
        ElseIf base = "ct" Or base = "ag" Then
            d1 = d1 - 1.3
        ElseIf base = "ga" Or base = "tc" Then
            d1 = d1 - 2.17
        ElseIf base = "cg" Then
            d1 = d1 - 2.24
        ElseIf base = "gc" Then
            d1 = d1 - 1.84
        ElseIf base = "gg" Or base = "cc" Then
            d1 = d1 - 1.42
        End If
    Next i
    base = Mid(s1, SeqLen, 1)
    If base = "a" Or base = "t" Then
        d1 = d1 + 0.98
    Else
        d1 = d1 + 1.03
    End If
dGCalc = d1
On Error Go To 0
Exit Function
dGCalc_Error:
    MsgBox "Error" & Err.Number & " ("& Err.Description & ") in
procedure dGCalc of Module XRAYString Line Number " & Erl
End Function
```

Apparatus

As should be apparent, certain embodiments employ processes involving data stored in or transferred through one or more computer systems or other processing systems. Embodiments of the invention also relate to apparatus for performing these operations. This apparatus may be specially constructed for the required purposes, or it may be a general-purpose computer (or a collection on networked computers) selectively activated or reconfigured by a computer program and/or data structure stored in the computer.

In addition, embodiments of the present invention relate to computer readable media or computer program products that include program instructions and/or data (including data structures) for performing various computer-implemented operations. Examples of computer-readable media include, but are not limited to, magnetic media such as disk drives, semiconductor memory devices, magnetic tape, optical media such as CDs, magneto-optical media, and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Figure 2:
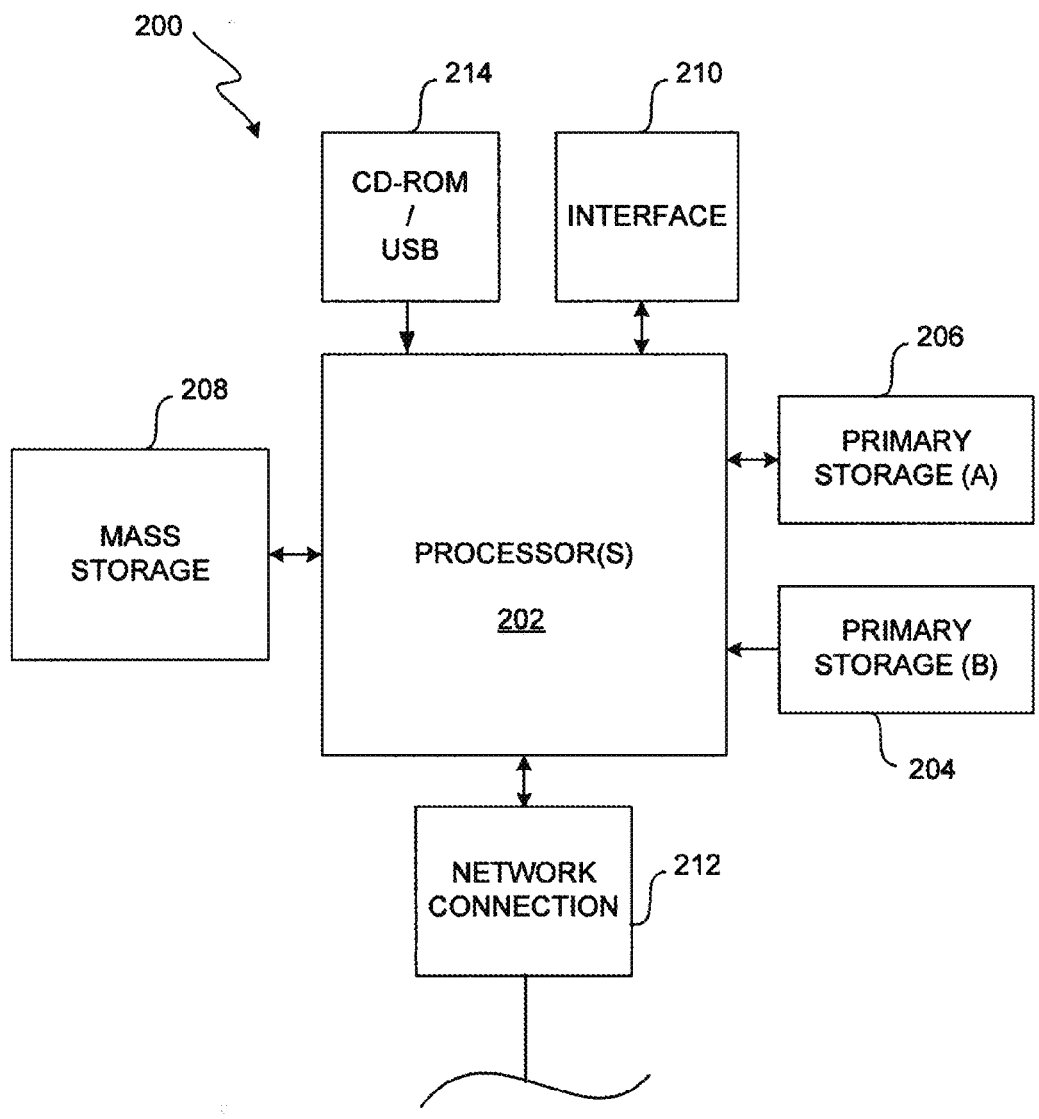
FIG. 2 is a schematic diagram of apparatus that may be employed to implement various embodiments described herein.

FIG. 2 illustrates a typical computer system that, when appropriately configured or designed, can serve as an analysis apparatus of this invention. The computer system 200 includes any number of processors 202 (also referred to as central processing units, or CPUs) that are coupled to storage devices including primary storage 206 (typically a random access memory, or RAM), primary storage 204 (typically a read only memory, or ROM). CPU 202 may be of various types including microcontrollers and microprocessors such as programmable devices (e.g., CPLDs and FPGAs) and unprogrammable devices such as gate array ASICs or general purpose microprocessors. As is well known in the art, primary storage 204 acts to transfer data and instructions to the CPU and primary storage 206 is used typically to transfer data and instructions in a bi-directional manner. Both of these primary storage devices may include any suitable computer-readable media such as those described above. A mass storage device 208 is also coupled bi-directionally to CPU 202 and provides additional data storage capacity and may include any of the computer-readable media described above. Mass storage device 208 may be used to store programs, data and the like and is typically a secondary storage medium such as a hard disk. It will be appreciated that the information retained within the mass storage device 208, may, in appropriate cases, be incorporated in standard fashion as part of primary storage 206 as virtual memory. A specific mass storage device such as a CD-ROM 214 may also pass data uni-directionally to the CPU.

CPU 202 is also coupled to an interface 210 that connects to one or more input/output devices such as such as video monitors, mice, keyboards, microphones, touch-sensitive displays, transducer card readers, tablets, styluses, voice or handwriting recognizers, or other well-known input devices such as, of course, other computers. Finally, CPU 202 optionally may be coupled to an external device such as a database or a computer or telecommunications network using an external connection as shown generally at 212. With such a connection, it is contemplated that the CPU might receive information from the network, or might output information to the network in the course of performing the method steps described herein.

Sequence or other data, can be input into a computer by a user either directly or indirectly. In one embodiment, the computer system 200 is directly coupled to a sequencing tool that reads and/or analyzes sequences of amplified nucleic acids. Sequences or other information from such tools are provided via interface 212 for analysis by system 200. Alternatively, the sequences processed by system 200 are provided from a sequence storage source such as a database or other repository. Once in the processing apparatus 200, a memory device such as primary storage 206 or mass storage 208 buffers or stores, at least temporarily, sequences of the nucleic acids. In addition, the memory device may store tag numbers for various chromosomes or genes, calculated copy counts, etc. The memory may also store various routines and/or programs for analyzing the presenting the sequence or mapped data. Such programs/routines may include programs for performing statistical analyses, etc.

In one example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. As indicated, the computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user (or apparatus) who will analyze and/or store the data. Transmittal can occur via the internet, but can also occur via satellite or other connection. Alternately, data can be stored on a computer-readable medium (e.g., CD or semiconductor memory storage device) and the medium can be shipped to an end user (e.g., via mail). The remote user can be in the same or a different geographical location including, but not limited to a building, city, state, country or continent.

In some embodiments, the methods of the invention further comprise collecting data regarding a plurality of polynucleotide sequences and sending the data to a computer. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet.

In one aspect, the invention further provides a system capable or performing quantitative analysis of nucleotide sequencing with a precision of at least 60%, 65%, 70%, 75%, 80%, 85%, 90%, 91%, 92%, 93%, 94%, 95%, 96%, 97%, 98%, or at least 99%. The nucleotide sequencing can comprise Sanger sequencing, massively parallel sequencing, hybridization or other techniques as described herein. The system can comprise various components, e.g., laboratory equipment and computer systems, and can be configured to carry out the methods of the invention disclosed herein.

EXAMPLES

Example 1

Effect of GC Content on Number of Sequences Observed

Figure 3:
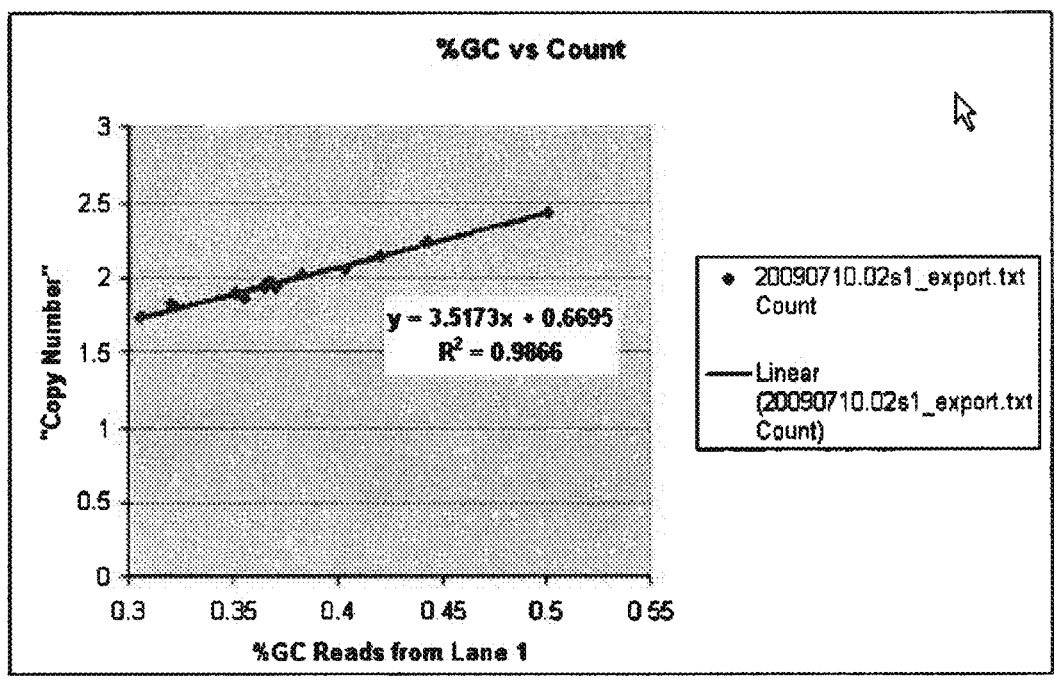
FIG. 3 is a graph illustrating that combining GC content and experiment sequence sampling patterns (modeled as average GC per lane per chromosome) accounts for significant variability. Each point represents the length normalized count frequency on a chromosome in an Illumina Genome Analyzer lane. The x-axis is the average GC fraction for the sequencing lane and the y-axis is the length/sequencing depth normalized count frequency.

FIG. 3 shows the strong effect of sequence GC content on the number of experimentally generated sequences match difference chromosomes. The data underlying the figure should show equal copy number of all chromosomes. However, the experimental procedure is biased so that sequences with lower GC content are observed less frequently than sequences with higher GC content. This GC bias amplifies or attenuates the signal of chromosomal regions independently of their true biological abundance.

Example 2

GC Content Variation between Samples

Figure 4:
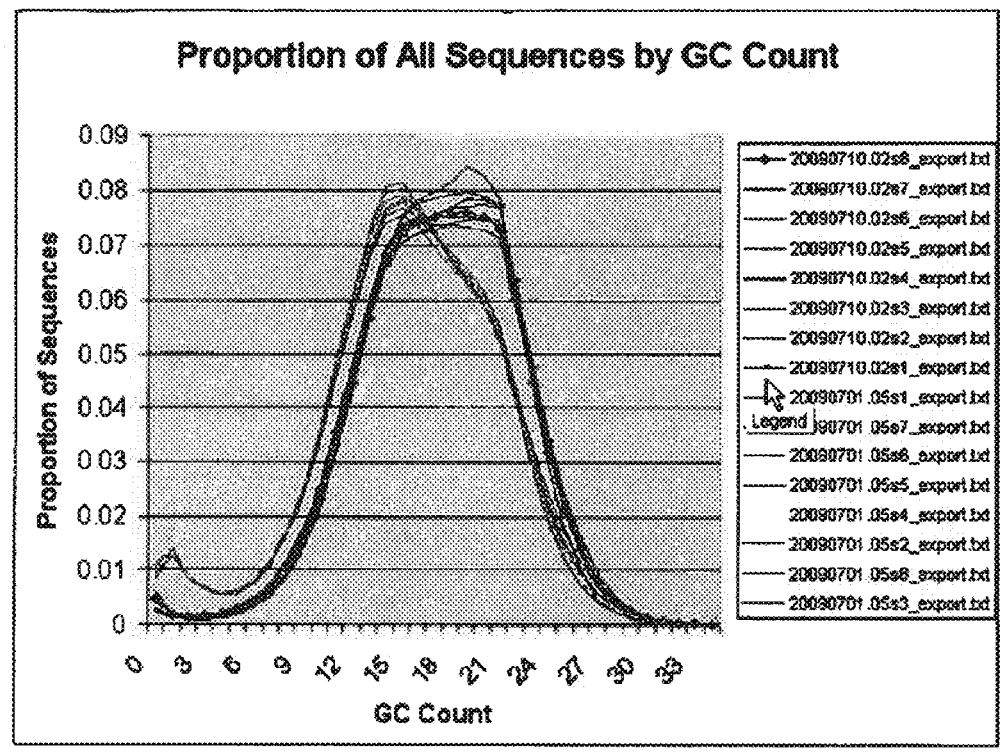
FIG. 4 is a graph illustrating that the GC content of generated sequences differs between two different experiments.

If the GC content of chromosome regions that match the generated sequences in each experiment were uniform, chromosomal GC content could be used to normalize data and provide basal copy number estimates centered at 2.0. However, this is not the case. FIG. 4 is a graph showing the DNA sequenced in two separate experiments has varying GC content (gray versus black). Normalizing the inter-experimental data by a constant (i.e., the GC content per chromosome) would not correct for this bias.

Example 3

Correcting Observed Number of Chromosomes for GC Content

Figure 5:
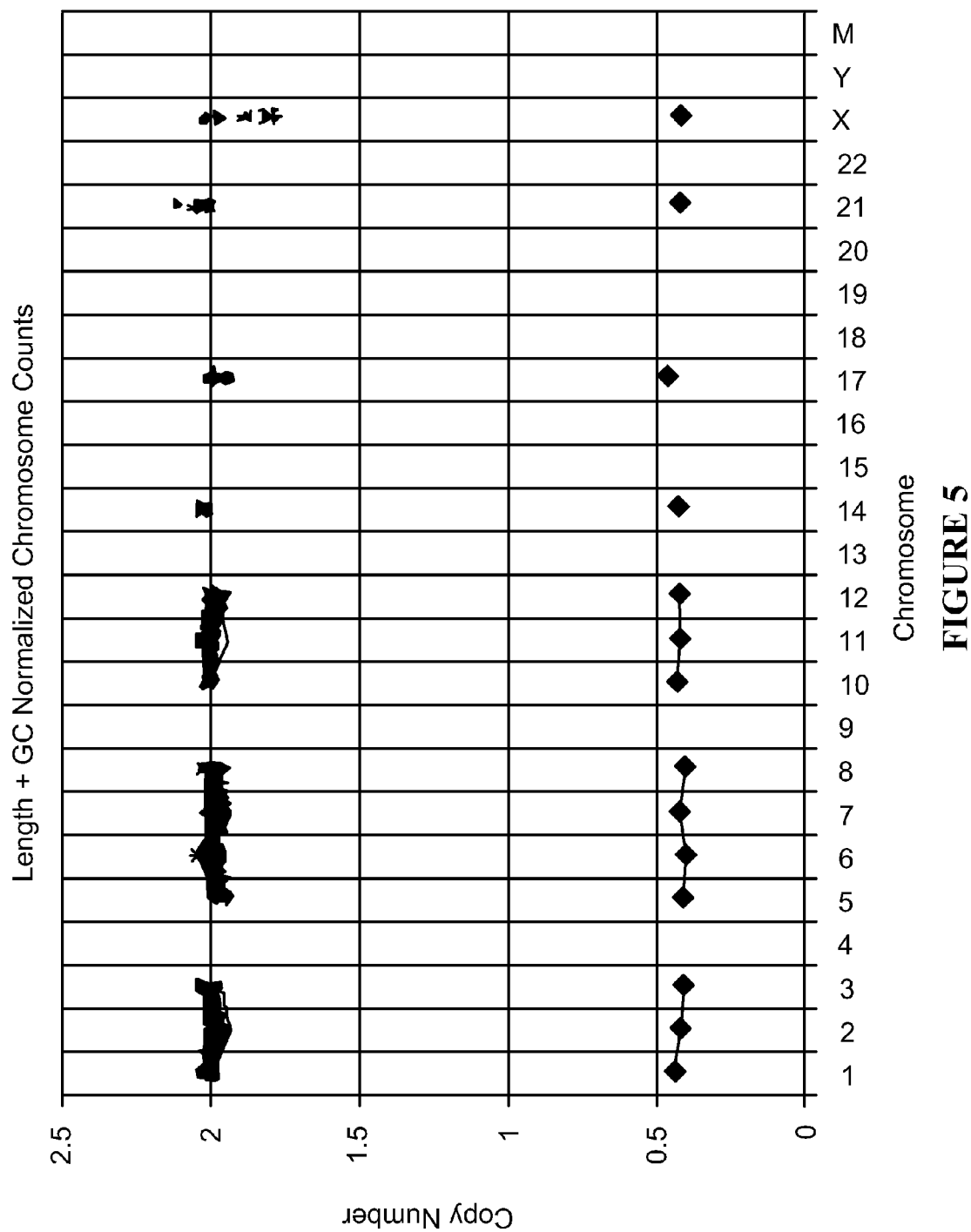
FIG. 5 illustrates normalizing using the coverage (sampling) patterns of the sequences results in consistent copy number estimates between experiments (gray and black). A drop seen in some chromosome X counts corresponds to cases where the fetus is male and the single high point for chromosome 21 corresponds to a clinically verified case of trisomy 21.

The method of the invention can correct for both intra and inter experimental bias. FIG. 5 shows that consistent copy number estimates that can be compared between experiments result after the chromosome base sampling pattern of the experiment runs is accounted for. The data is this figure is normalized by the GC content of each individual sequence tag instead of the entire chromosome that each sequence tag maps to.

The data was generated as follows. Upon completion of sequencing of a sample by the Illumina Genome Analyzer II (Illumina Inc., San Diego, Calif., USA), the Illumina "Sequencer Control Software" transferred image and base call files to a Unix server running the Illumina "Genome Analyzer Pipeline" software version 1.4. The Illumina "Gerald" program was run to align sequences to the reference Human genome from the National Center for Biotechnology Information (NCBI v36, available at ncbi|.|nlm|.|nih|.|gov).

Obtaining Chromosome Copy Number Estimates: Each sample was processed individually to obtain chromosome copy number estimates.

The sequences from above that uniquely aligned to the genome were read from Gerald output (export.txt files) by a program running on a computer running the Windows operating system. After sequence alignments with identical start and end coordinates were removed, a length normalized copy number estimate for each chromosome, say, chromosome i, was generated via the formula:

$$CN1(i)=2*(n(i)*\text{tot\_len})/(N*\text{len}(i)) \qquad \text{(Equation 12)}$$

where:
CN1(i) is the copy number of chromosome i;
n(i) is the number of alignments to chromosome
i tot_len=the total length in bases for the genome under consideration
N=the total number of alignments; and
len(i) is the length in bases of chromosome i.

Correcting Chromosome Copy Number Estimates:
Each chromosome copy number estimate was corrected for GC content.

$$CN2(i)=CN1(i)+2-G(gc(i)) \qquad \text{[Equation 2]}$$

where:
CN1 is defined in Equation 1 above;
CN2(i) is the corrected copy number of chromosome i;
gc(i) is the average GC content of sequences aligned to chromosome i; and
G(x) is the regression line fitted to the series (gc(i),CN1(i)).

The regression line can be fit using linear, exponential, or other function.

FIG. 5 shows one data point, CN2(i) per chromosome per analyzed sample. The single, outlier point on chromosome 21 is a T21 case and the lower chromosome X points are from mothers bearing male embryos.

Example 4

GC Partitioning to Correct Observed Number of Chromosomes

Studies on maternal blood samples show that, even without transformation into a modified Z-score, the GC normalization as performed using the partitioning of Equation 3 provides excellent discrimination between normal and aneuploidy cases (FIG. 6). Calculated count numbers are shown on separate rows for each of various human chromosomes. In other words, each row represents a different chromosome. Results for subjects with trisomy 18 are shown in columns 10-12; for subjects with trisomy 13 are shown in columns 12-14; and for subjects with trisomy 21 are shown in columns 15-20.

Note that the values are higher for trisomies than all other counts in the same row. Note also that errors were found in the scores reported in row "18" at the fourth, fifth, and eleventh columns. The reported data is for normal cases but are shown to be higher than aneuploidy cases. These mistakes were caused by a single sample that was later found to have been subjected to faulty processing.

One potential issue seen from FIG. 6 is that even though the count scores can discriminate normal and aneuploidy cases, different chromosomes have differing scale and center. Cutoff thresholds for calling aneuploidy must be empirically and individually selected for each chromosome (R) of interest. Also, levels of different chromosomes cannot be directly compared. The Modified z-scores derived from the GC normalized score scores that also provide excellent discrimination, are normally distributed, give cross-chromosome comparable scores.

Use of the GC normalized score on real maternal plasma sequencing data shown in FIG. 7 indicate that a modified z-score of GC partition normalized counts (from Equation 7) works well. On the x-axis different samples are presented and on the y-axis z-score results for those samples are depicted. Samples with a chromosome 11 deletion, as well as samples with trisomies are shown in the right portion of the graph.

When the embryo is male, chromosome X levels (horizontal lines well below zero) are markedly depressed. Cases where inspection of karyograms identify chromosome 11 deletion (in the D11 column), chromosome 13 amplification (in the T13 columns), chromosome 18 amplification (in the T18 columns), and chromosome 21 amplification (in the T21 columns) lie outside of the two sided 0.001 standard normal critical level (dotted horizontal lines). All the normal samples fall between the dotted lines. Training data was a subset of the normal cases shown. The figure shows that one chromosome 18 case was not identified. Further investigation revealed a problem with the sample. Five million generated sequences per sample were used to calculate scores.

Other Embodiments

Although the above has generally described the present invention according to specific processes and apparatus, the present invention has a much broader range of applicability. In particular, the present invention has been described in terms of detecting aberrations in DNA or other biological samples, but is not so limited, as the concepts and methods presented herein may also be applied in other contexts such as testing and measurements taken on inorganic systems. Of course, those of ordinary skill in the art will recognize other variations, modifications, and alternatives.

What is claimed is:

1. A method of detecting aneuploidy or sex in a fetus, the method comprising:
    (a) extracting DNA from the blood of an individual carrying the fetus;
    (b) mapping segments of the extracted DNA to a reference genome comprising a chromosome of interest;
    (c) partitioning the segments of the extracted DNA and partitioning substrings of a part or the entirety of the reference genome into a plurality of partition levels based on the level of a source of variability, wherein the source of variability biases the number of segments mapped to the reference genome, and wherein the part or the entirety of the reference genome includes the chromosome of interest;
    (d) calculating an expected number of segments mapped to the chromosome of interest,
        wherein
        the calculating comprises summing products over a range of partition levels, each product for a partition level comprising (i) the number of segments generated from the extracted DNA mapped to the part or the entirety of the reference genome, and (ii) the ratio of the number of substrings in the chromosome of interest over the number of substrings in the part or the entirety of the reference genome, and
        the expected number of segments is based on an assumption about chromosome type and number; and
    (e) detecting aneuploidy or sex in the fetus by comparing an actual number of segments mapped to the chromosome of interest against the expected number of segments mapped to the chromosome of interest.

2. The method of claim 1, wherein mapping the segments of the extracted DNA is conducted without distinguishing maternal and fetal origin DNA.

3. The method of claim 1, wherein the source of variability is the GC content of the segments.

4. The method of claim 1, wherein the source of variability reflects the ease with which the segments are amplified by an amplification technique applied to the extracted DNA.

5. The method of claim 1, wherein calculating the expected number of segments mapped to the chromosome of interest consists of summing products over a range of partition levels as in the following expression:

$$E(\#R) = \sum_{\forall i \in P(G)} n_i \cdot \frac{|R_i|}{|G_i|}$$

wherein
E(#R) is the expected number of segments mapped to the chromosome of interest,
P(G) is all partition levels in the genome,
$n_i$ is the number of the segments generated from the extracted DNA mapped to the part or the entirety of the reference genome assigned to a partition i,
$|R_i|$ is the number of the substrings in the chromosome of interest that are assigned to partition i, and
$|G_i|$ is the number of the substrings in the part or the entirety of the reference genome that are assigned to partition i.

6. The method of claim 1, wherein the partition levels are different amounts of GC content in the segments.

7. The method of claim 1, wherein the segments all have the same length.

8. The method of claim 7, wherein the segments all have a length of at least 30 base pairs.

9. The method of claim 1, wherein the detecting aneuploidy or sex in the fetus comprises providing the comparison of the actual number of segments mapped to the chromosome of interest against the expected number of segments mapped to the chromosome of interest in the form of a z-score.

10. The method of claim 1, wherein the detecting aneuploidy or sex in the fetus comprises providing the comparison of the actual number of segments mapped to the chromosome of interest against the expected number of segments mapped to the chromosome of interest in a form that includes trained parameters.

11. The method of claim 10, wherein the trained parameters are obtained from samples taken from females carrying fetuses without aneuploidy.

12. The method of claim 11, wherein the trained parameters comprise a sample center and a sample spread.

13. The method of claim 1, further comprising performing an internal control by comparing a count or score of the segments mapped to the chromosome of interest against a different count or score of the segments mapped to a different chromosome.

14. The method of claim 1, further comprising PCR amplifying the segments before mapping in (b).

15. The method of claim 1, wherein the mapping in (b) comprises performing Sanger sequencing, massively parallel sequencing, and/or hybridization of segments from the extracted DNA.

16. The method of claim 1, wherein the segments all have a length of at least 20 base pairs.

17. The method of claim 1, further comprising sequencing the extracted DNA to produce the segments of extracted DNA.

18. A computer program product comprising a non-transitory machine readable medium on which is provided program code that, when executed by one or more processors of a computer system, causes the computer system to implement a method for detecting aneuploidy or sex in a fetus, the program code comprising:
(a) code for receiving sequence information for segments of DNA extracted from the blood of an individual carrying the fetus;
(b) code for mapping the segments of DNA to a reference genome comprising a chromosome of interest;
(c) code for partitioning the segments of the extracted DNA and partitioning substrings of a part or the entirety of the reference genome into a plurality of partition levels based on the level of a source of variability, wherein the source of variability biases the number of segments mapped to the reference genome, and wherein the part or the entirety of the reference genome includes the chromosome of interest;
(d) code for calculating an expected number of segments mapped to the chromosome of interest,
wherein
the calculating comprises summing products over a range of partition levels, each product for a partition level comprising (i) the number of segments generated from the extracted DNA mapped to the part or the entirety of the reference genome, and (ii) the ratio of the number of substrings in the chromosome of interest over the number of substrings in the part or the entirety of the reference genome, and
the expected number of segments is based on an assumption about chromosome type and number; and
(e) code for detecting aneuploidy or sex in the fetus by comparing an actual number of segments mapped to the chromosome of interest against the expected number of segments mapped to the chromosome of interest.

19. The computer program product of claim 18, wherein the code for mapping the segments of the extracted DNA comprises code for conducting the mapping without distinguishing maternal and fetal origin DNA.

20. The computer program product of claim 18, wherein the source of variability is the GC content of the segments.

21. The computer program product of claim 18, wherein the source of variability reflects the ease with which the segments are amplified by an amplification technique applied to the extracted DNA.

22. The computer program product of claim 18, wherein calculating the expected number of segments mapped to the chromosome of interest consists of summing products over a range of partition levels as in the following expression:

$$E(\#R) = \sum_{\forall i \in P(G)} n_i \cdot \frac{|R_i|}{|G_i|}$$

wherein
E(#R) is the expected number of segments mapped to the chromosome of interest,
P(G) is all partition levels in the genome,
$n_i$ is the number of the segments generated from the extracted DNA mapped to the part or the entirety of the reference genome assigned to a partition i,
$|R_i|$ is the number of the substrings in the chromosome of interest that are assigned to partition i, and
$|G_i|$ is the number of the substrings in the part of the entirety of the reference genome that are assigned to partition i.

23. The computer program product of claim 18, wherein the partition levels are different amounts of GC content in the segments.

24. The computer program product of claim 18, wherein the segments all have the same length.

25. The computer program product of claim 24, wherein the segments all have a length of at least 30 base pairs.

26. The computer program product of claim 18, wherein the code for detecting aneuploidy or sex in the fetus comprises code for providing the comparison of the actual number of segments mapped to the chromosome of interest against the expected number of segments mapped to the chromosome of interest in the form of a z-score.

27. The computer program product of claim 18, wherein the code for detecting aneuploidy or sex in the fetus comprises code for providing the comparison of the actual number of segments mapped to the chromosome of interest against the expected number of segments mapped to the chromosome of interest in a form that includes trained parameters.

28. The computer program product of claim 27, wherein the trained parameters are obtained from samples taken from females carrying fetuses without aneuploidy.

29. The computer program product of claim 28, wherein the trained parameters comprise a sample center and a sample spread.

30. The computer program product of claim 18, further comprising code for performing an internal control by comparing segments or a count or score of the segments mapped to the chromosome of interest against a different count or score of the segments mapped to a different chromosome of the extracted DNA.

31. The computer program product of claim 18, wherein the segments all have a length of at least 20 base pairs.

32. The computer program product of claim 18, further comprising code for sequencing the DNA extracted from the blood of an individual carrying the fetus to produce the sequence information for segments of the DNA.

* * * * *